United States Patent
Suzuki et al.

(10) Patent No.: US 7,365,106 B2
(45) Date of Patent: Apr. 29, 2008

(54) CATIONICALLY CURABLE COMPOSITION FOR DENTAL USE

(75) Inventors: Takeshi Suzuki, Tokyo (JP); Hideki Kazama, Tokyo (JP)

(73) Assignees: Tokuyama Corporation, Shunan-shi (JP); Tokuyama Dental Corporation, Tokyo (JP)

( * ) Notice: Subject to any disclaimer, the term of this patent is extended or adjusted under 35 U.S.C. 154(b) by 326 days.

(21) Appl. No.: 11/114,086

(22) Filed: Apr. 26, 2005

(65) Prior Publication Data

US 2005/0250868 A1    Nov. 10, 2005

(30) Foreign Application Priority Data

Apr. 27, 2004  (JP) ............... 2004-131431
Jun. 29, 2004  (JP) ............... 2004-191380

(51) Int. Cl.
*C08F 2/46*    (2006.01)
*A61K 6/08*    (2006.01)
*A61K 6/087*   (2006.01)
*A61C 5/00*    (2006.01)

(52) U.S. Cl. ............ 522/168; 522/170; 522/178; 522/181; 522/15; 522/16; 522/17; 522/25; 522/27; 522/31; 522/26; 523/114; 523/115; 523/116; 523/117; 523/118; 523/120; 433/228.1; 433/215; 433/226; 433/229

(58) Field of Classification Search .......... 522/15, 522/16, 17, 25, 26, 27, 31, 170, 168, 178, 522/181; 523/114–120; 433/228.1, 215, 433/226, 229

See application file for complete search history.

(56) References Cited

U.S. PATENT DOCUMENTS 5,395,862 A *  3/1995  Neckers et al. ............. 522/25
5,639,802 A *  6/1997  Neckers et al. ............. 522/25
5,885,837 A *  3/1999  Winkler et al. ............ 435/91.1
6,610,759 B1 *  8/2003  Chappelow et al. ......... 522/25
6,765,036 B2 *  7/2004  Dede et al. ................ 522/15
6,930,134 B2 *  8/2005  Suzuki et al. .............. 522/25
2004/0186195 A1 *  9/2004  Suzuki et al. .............. 522/31

FOREIGN PATENT DOCUMENTS

| EP | 0 897 710 A2 | 2/1999 |
| EP | 0 927 726 A1 | 7/1999 |
| EP | 1 422 254 A2 | 5/2004 |
| EP | 1 431 315 A2 | 6/2004 |
| JP | 11-130945 A | 5/1999 |
| JP | 2004196949 A * | 7/2004 |

* cited by examiner

*Primary Examiner*—Sanza L. McClendon
(74) *Attorney, Agent, or Firm*—Birch, Stewart, Kolasch & Birch, LLP

(57) ABSTRACT

A cationically curable composition for dental use containing a cationic polymerization initiator (I) and cationically polymerizable monomers (II), the cationically polymerizable monomers (II) containing an oxetane compound and an epoxy compound or an alkenyl ether compound at a ratio of amounts that satisfy the conditions expressed by the following formula, $$(a \times A):(b \times B) = 91:9 \text{ to } 45:55$$

wherein A is a mol number of the oxetane compound, "a" is an average number of the oxetane functional group contained in one molecule of the oxetane compound, B is a mol number of the epoxy compound or the alkenyl ether compound, and "b" is an average number of the epoxy functional group contained in one molecule of the epoxy compound or an average number of the alkenyl ether functional group contained in one molecule of the alkenyl ether compound.

The composition is not hindered by oxygen from being polymerized, cures quickly even without using a special polymerizable monomer or a particular polymerization initiator, little forms an unpolymerized layer on the surface even when polymerized and cured in a highly humid environment such as in the oral cavity, and is suited as a filling/restorative material for dental use.

6 Claims, No Drawings

CATIONICALLY CURABLE COMPOSITION FOR DENTAL USE

BACKGROUND OF THE INVENTION

1. Field of the Invention

The present invention relates to a dental material and, particularly, to a cationically curable composition that can be favorably used as a filling/restorative material for dental use.

2. Description of the Related Art

A tooth that is damaged due to decaying or breakage is usually restored by using a photo-curable composite filling/restorative material which is called composite resin owing to its easy operation and a high degree of aesthetic appearance. This composite resin usually comprises a polymerizable monomer, a filler and a polymerization initiator. As the polymerizable monomer, there has been used a (meth)acrylate type radically polymerizable monomer owing to its favorable photo-polymerizing property.

In the dental therapy, a high degree of aesthetic appearance is an important requirement. In many cases, in general, a dental composite resin is used in a manner of being filled in the oral cavity and is, then, cured. Here, if the color tone greatly changes before and after the curing, the color tone may change after curing making it difficult to obtain a favorable aesthetic appearance though the color might have been in agreement with that of the neighboring teeth at the time of being filled (before curing) (if ΔE* that represents the degree of discoloration is not larger than 1.5, it has been said that the discoloration cannot usually be perceived by naked eyes). In addition to aesthetic appearance immediately after the therapy, it is further requested that the aesthetic appearance does not wane even after the use. For instance, it is necessary to avoid such an occurrence that the dental material used in the oral cavity easily undergoes the discoloration or is colored due to various coloring substances stemming from the foods.

However, the radically polymerizable monomer is hindered by oxygen from being polymerized. When the radically polymerizable monomer is polymerized and cured in the oral cavity, therefore, an unpolymerized layer or a layer polymerized to a low degree remains on the surface posing a problem in that the unpolymerized layer is colored/discolored with the passage of time making it difficult to obtain a satisfactory aesthetic appearance. After the curing, therefore, the unpolymerized layer must be removed by polishing.

Besides, the radically polymerizable monomers are usually of the type of addition polymerization leaving a problem of an essentially large coefficient of contraction.

To polymerize and cure the filling/restorative material such as the composite resin after filled in the cavity of a tooth that must be restored, the filling/restorative material that is filled must be irradiated with light and the polymerization starts from the surface thereof, i.e., from a position remote from the dentin. Due to the contraction by polymerization, however, stress is produced causing the filling/restorative material to exfoliate from the dentin, and a gap tends to develop between the tooth and the filler/restorative material. To cope with the stress produced by the contraction by polymerization, there have been proposed adhesives or dental use that produce very strong adhesion. However, the state of the tooth varies depending upon the individuals or depending upon the teeth even in the same person. Even by using such dental adhesives, therefore, perfect adhesion is not, in practice, obtained for all teeth. Therefore, it has also been desired to develop a dental composite resin which contracts in amounts as small as possible when polymerized and does not develop a gap despite the adhering force may not be very large depending upon the condition of the tooth. To obtain a large adhering force, further, the above adhesive requires a complex technology boosting the cost. Therefore, it has been desired to simplify the use.

As the polymerizable monomers of which the polymerization is not hindered by oxygen, there can be exemplified alkenyl ether compounds as represented by vinyl ether and 1-propenyl ether, as well as cationically polymerizable monomers such as epoxide and oxetane which are cyclic ether compounds (prior art 1 appearing later).

Among them, alkenyl ethers undergo the polymerization and curing very quickly accompanied, however, by a problem of being colored after curing. Like the (meth)acrylate compounds, further, the alkenyl ethers are vinyl monomers of the addition polymerization type and undergo the contraction by polymerization to a large extent.

On the other hand, the epoxy compounds and the oxetane compounds are the ring opening-polymerizable compounds which, after curing, are colored very little compared to the alkenyl ethers and, besides, are contracted considerably little by polymerization. It has therefore been proposed to use these components for dental curable compositions that must satisfy the requirements of a high degree of aesthetic appearance and a small contraction by polymerization as described above (see, for example, prior arts 2 to 7 appearing later).

However, the epoxy functional group polymerizes slowly as compared with the alkenyl ether functional group, and is not suited for the dental applications where quick polymerization and curing are required in the oral cavity.

On the other hand, the oxetane functional group has been regarded to be polymerized quicker than the epoxy functional group. Like other cationically polymerizable monomers, however, the oxetane functional group essentially has a problem of subject to be hindered by water from being polymerized. When used in the oral cavity, therefore, the oxetane functional group tends to form an unpolymerized layer on the surface still leaving room for improvement.

Study has been forwarded extensively concerning the cationically polymerizable monomers even in the fields other than the dental use, and there have been proposed a technology that uses an oxetane compound of a special structure (e.g., prior art 8) and a technology that uses a particular polymerization initiator (e.g., prior art 9) in order to solve the above problem in that the polymerization is hindered by water.

Prior Art 1: Radotech Academy, "Present Status of UV•EV Curing Technology and its Prospect", CMC Publishing Co., Dec. 27, 2002, pp 45-48.
Prior Art 2: JP-T-10-508067
Prior Art 3: JP-A-11-130945
Prior Art 4: JP-T-2001-520758
Prior Art 5: JP-T-2001-520759
Prior Art 6: JP-A-8-245783
Prior Art 7: JP-A-2004-149587
Prior Art 8: JP-A-2004-91553
Prior Art 9: JP-A-2004-91698

SUMMARY OF THE INVENTION

It is therefore an object of the present invention to provide a cationically curable composition for dental use which is not hindered by oxygen from being polymerized, is quickly cured without using any special polymerizable monomer or particular polymerization initiator, little forms an unpolymerized layer on the surface even when polymerized and cured in a highly humid environment such as in the oral cavity, contracts very little when polymerized, is capable of forming a cured body featuring excellent aesthetic appearance, and can be favorably used as a dental filling/restorative material.

In order to solve the above problems, the present inventors have conducted keen study, discovered that when an oxetane compound and an epoxy compound or an alkenyl ether compound are used as the cationically polymerizable monomers in such a combination that satisfies a predetermined ratio of amounts, the polymerization thereof is affected by water far less than when they are used alone, suppressing a change in the color tone before and after the curing, making it possible to obtain a cured body featuring excellent aesthetic appearance, and have finished the invention.

According to the present invention, there is provided a cationically curable composition for dental use containing a cationic polymerization initiator (I) and cationically polymerizable monomers (II), wherein the cationically polymerizable monomers (II) contain an oxetane compound having an oxetane functional group in the molecule thereof and an epoxy compound having an epoxy functional group in the molecule thereof or an alkenyl ether compound having an alkenyl ether functional group in the molecule thereof at a ratio of amounts that satisfy the conditions expressed by the following formula, $$(a \times A):(b \times B)=91:9 \text{ to } 45:55$$

wherein A is a mol number of the oxetane compound, "a" is an average number of the oxetane functional group contained in one molecule of the oxetane compound, B is a mol number of the epoxy compound or the alkenyl ether compound, and "b" is an average number of the epoxy functional group contained in one molecule of the epoxy compound or an average number of the alkenyl ether functional group contained in one molecule of the alkenyl ether compound.

The cationically curable composition for dental use of the present invention uses the oxetane compound and the epoxy compound or the alkenyl ether compound as the cationically polymerizable monomers (II) in amounts of such a ratio that the ratio of the oxetane functional group and the epoxy functional group or the alkenyl ether functional group lies within a predetermined range. As compared to the dental materials using the conventional (meth)acrylate type radically polymerizable monomers, therefore, the cationically curable composition for dental use of the present invention contracts very little when it is polymerized and is not hindered by oxygen from being polymerized. Further, since it cures within short periods of time, use of the cationically curable composition in the oral cavity does not cause a large burden Lo the patient. Besides, the cationically curable composition is little hindered by water from being polymerized, does not almost change the color tone before and after the curing, and provides a cured body featuring excellent aesthetic appearance.

DETAILED DESCRIPTION OF THE INVENTION

The cationically curable composition for dental use of the present invention contains a cationic polymerization initiator (I) and cationically polymerizable monomers (II) as essential components, and is, as required, blended with other types of polymerizable monomers, a filler (III) as well as various additives.

Cationic Polymerization Initiator (1)

There is no particular limitation on the cationic polymerization initiator (I) that is used in the present invention, and any known cationic polymerization initiator may be used. As the cationic polymerization initiator, there can be used Lewis acid or Bronsted acid, or a compound that forms Lewis acid or Bronsted acid upon being heated or being irradiated with light. It is particularly desired to use, as the cationic polymerization initiator (I), a so-called photo acid generator that forms Lewis acid or Bronsted acid upon being irradiated with light from the standpoint of quick and easy polymerization in such an environment as in the oral cavity.

As the photo acid generator, there can be used a diaryliodonium salt compound, sulfonium salt compound, sulfonic acid ester compound and halomethyl-substituted-5-triazine derivatives. Among them, the diaryliodonium salt compound and the sulfonium salt compound are excellent in regard to their particularly high polymerizing activity.

Concrete examples of the diaryliodonium salt compound include those containing the Following cations and anions:

Cations:
diphenyliodonium,
bis(p-chlorophenyl)iodonium,
ditolyliodonium,
bis(p-tert-butylphenyl)iodonium,
p-isopropylphenyl-p-methylphenyliodonium,
bis(m-nitrophenyl)iodonium,
p-tert-butylphenylphenyliodonium,
p-methoxyphenylphenyliodonium,
bis(p-methoxyphenyl)iodonium,
p-octyloxyphenylphenyliodonium,
p-phenoxyphenylphenyliodonium, and
bis(p-dodecylphenyl)iodonium.

Anions:
chloride,
bromide,
p-toluenesulfonato,
trifluoromethanesulfonato,
tetrafluoroborate,
tetrakispentafluorophenylborate,
tetrakispentafluorophenylgallate,
hexafluorophosphate,
hexafluoroarsenato, and
hexafluoroantimonate.

Among the diaryliodonium salt compounds containing the above cations and anions according to the present invention, it is desired to use those having, as an anion, p-toluenesulfonato, trifluoromethanesulfonato, tetrafluoroborate, tetrakispentafluorophenylborate, tetrakispentafluorophenyl-gallate, hexafluorophosphate, hexafluoroarsenato or hexafluoroantimonate from the standpoint of solubility in the polymerizable monomer. In a state where the nucleophilic property is low and no light is irradiated, there can be preferably used those having, as an anion, hexafluoroantimonate, tetrakispentafluorophenylborate or tetrakispentafluorophenyl-gallate since it can be stably preserved as a mixture with the polymerizable monomer (II) that will be described later.

As the sulfonium salt compound that can be favorably used as a photo acid generator, there can be exemplified those having the following cations and anions:

Cations:
dimethylphenacylsulfonium,
dimethylbenzylsulfonium,
dimethyl-4-hydroxyphenylsulfonium,
dimethyl-4-hydroxynaphthylsulfonium,
dimethyl-4,7-dihydroxynaphthylsulfonium, dimethyl-4,8-dihydroxynaphthylsulfonium,
triphenylsulfonium,
p-tolyldiphenylsulfonium,
p-tert-butylphenyldiphenylsulfonium, and
diphenyl-4-phenylthiophenylsulfonium.
 Anions:
chloride,
bromide,
p-toluenesulfonato,
trifluoromethanesulfonato,
tetrafluoroborate,
tetrakispentafluorophenylborate,
tetrakispentafluorophenylgallate,
hexafluorophosphate,
hexafluoroalcenato, and
hexafluoroantimonate.

The above variety of photo acid generators can be used in a single kind or in a combination of two or more kinds. There is no particular limitation on the amount of the photo acid generator that is used provided the polymerization can be initiated by the irradiation with light. In order to accomplish both a suitable rate of polymerization and various properties (e.g., weather-proof property and hardness) of the cured body that is obtained, however, the photo acid generator is usually used in an amount of 0.001 to 10 parts by mass and, particularly, 0.05 to 5 parts by mass per 100 parts by mass of the cationically polymerizable monomers (II) that will be described later.

The above photo acid generator, usually, does not absorb light in the near ultraviolet to visible regions and, in many cases, requires a special source of light to initiate the polymerization reaction. It is, therefore, desired to add a compound that absorbs light in the near ultraviolet to visible region as a sensitizer to the above photo acid generator.

Examples of the compound that can be used as a sensitizer may be acridine dye, phenothiazine, benzoflavin dye, and fused polycyclic aromatic compounds such as anthracene and perylene. Among these sensitizers, it is desired to use fused polycyclic aromatic compounds owing to their favorable polymerization activity. Among them, it is desired to use a substituted group-containing fused polycyclic aromatic compound having a structure in which a saturated carbon atom having at least one hydrogen atom is bonded to a fused polycyclic aromatic ring.

Concrete examples of the substituted group-containing fused polycyclic aromatic compound include the following compounds:
1-methylnaphthalene,
1-ethylnaphthalene,
1,4-dimethylnaphthalene,
acenaphthene,
1,2,3,4-tetrahydrophenanthrene,
1,2,3,4-tetrahydroanthracene,
benzo[f]phthalan,
benzo[g]chroman,
benzo[g]isochroman,
N-methylbenzo[f]indolin,
N-methylbenzo[f]isoindolin,
phenalene,
4,5-dimethylphenanthrene,
1,8-dimethylphenanthrene,
acephenanthrene,
1-methylanthracene,
9-methylanthracene,
9-ethylanthracene,
9-cyclohexylanthracene,
9,10-dimethylanthracene,
9,10-diethylanthracene,
9,10-dicyclohexylanthracene,
9-methoxymethylanthracene,
9-(1-methoxyethyl)anthracene,
9-hexyloxymethylanthracene,
9,10-dimethoxymethylanthracene,
9-dimethoxymethylanthracene,
9-phenylmethylanthracene,
9-(1-naphthyl)methylanthracene,
9-hydroxymethylanthracene,
9-(1-hydroxyethyl)anthracene,
9,10-dihydroxymethylanthracene,
9-acetoxymethylanthracene,
9-(1-acetoxyethyl)anthracene,
9,10-diacetoxymethylanthracene,
9-benzoyloxymethylanthracene,
9,10-dibenzoyloxymethylanthracene,
9-ethylthiomethylanthracene,
9-(1-ethylthioethyl)anthracene,
9,10-bis(ethylthiomethyl)anthracene,
9-mercaptomethylanthracene,
9-(1-mercaptoethyl)anthracene,
9,10-bis(mercaptomethyl)anthracene,
9-ethylthiomethyl-10-methylanthracene,
9-methyl-10-phenylanthracene,
9-methyl-10-vinylanthracene,
9-allylanthracene,
9,10-diallylanthracene,
9-chloromethylanthracene,
9-bromomethylanthracene,
9-iodomethylanthracene,
9-(1-chloroethyl)anthracene,
9-(1-bromoethyl)anthracene,
9-(1-iodoethyl)anthracene,
9,10-dichloromethylanthracene,
9,10-dibromomethylanthracene,
9,10-diiodomethylanthracene,
9-chloro-10-methylanthracene,
9-chloro-10-ethylanthracene,
9-bromo-10-methylanthracene,
9-bromo-10-ethylanthracene,
9-iodo-10-methylanthracene,
9-iodo-10-ethylanthracene,
9-methyl-10-dimethylaminoanthracene,
aceanthrene,
7,12-dimethylbenz(a)anthracene,
7,12-dimethoxymethylbenz(a)anthracene,
5,12-dimethylnaphthacene,
cholanthrene,
3-methylcholanthrene,
7-methylbenzo(a)pyrene,
3,4,9,10-tetramethylperylene,
3,4,9,10-tetrakis(hydroxymethyl)perylene,
violanthrene,
isoviolanthrene,
5,12-dimethylnaphthacene,
6,13-dimethylpentacene,
8,13-dimethylpentaphene,
5,16-dimethylhexacene, and
9,14-dimethylhexaphene.

As the condensed polycyclic aromatic compounds other than those described above, there can be exemplified naphthalene, phenanthrene, anthracene, naphthacene, benz[a]anthracene, pyrene and perylene.

Among the above condensed polycyclic aromatic compounds according to the present invention, if good and bad to the living bodies are taken into consideration, it is desired to use a compound that initiates the polymerization with visible light, i.e., to use a compound that absorbs light in the visible region and, particularly, a compound that has a maximum absorption in the visible region. Further, the above condensed polycyclic aromatic compounds can be used either alone or in a combination of two or more kinds.

It is desired that the condensed polycyclic aromatic compound is used in an amount of 0.001 to 20 mols and, particularly, 0.005 to 10 mols per mole of the above-mentioned photo acid generator though the amount may differ depending upon the other components used in combination and the kind of the polymerizable monomers (II).

In the present invention, it is desired that an oxidizable photo radical generator is used together with the photo acid generator and the condensed polycyclic aromatic compound. By using the oxidizable photo radical generator, the polymerizing activity can be further increased. The oxidizable photo radical generator is the compound which is excited by the irradiation with light to generate radicals and of which the mechanism for generating the active radical species by excitation by the irradiation with light is created by the action of an oxidizing agent (the compounds themselves are reduced), like a radical generator of the type of so-called hydrogen-extracting type which forms radicals by extracting hydrogen atoms from a hydrogen donor relying upon the excitation, a self-cleaving type radical generator which is self-cleaved by the excitation to generate radicals, the radicals accepting electrons from the electron donor, or the one that is excited by the irradiation with light to directly accept electrons from the electron donor. As the oxidizable photo radical generators, there can be used any known compounds. However, it is desired to use photo radical generators of the hydrogen extracting type from such a standpoint that the polymerizing activity of when irradiated with light is higher than that of other compounds. Among them, it is particularly desired to use a diarylketone compound, an α-diketone compound or a ketocumarine compound. Concrete examples of the diarylketone compound, α-diketone compound and ketocumarine compound include the following compounds.

Diarylketone Compounds:
4,4-bis(dimethylamino)benzophenone,
9-fluorenone,
3,4-benzo-9-fluorenone,
2-dimethylamino-9-fluorenone,
2-methoxy-9-fluorenone,
2-chloro-9-fluorenone,
2,7-dichloro-9-fluorenone,
2-bromo-9-fluorenone,
2,7-dibromo-9-fluorenone,
2-nitro-9-fluorenone,
2-acetoxy-9-fluorenone,
benzanthrone,
anthraquinone,
1,2-benzanthraquinone,
2-methylanthraquinone,
2-ethylanthraquinone,
1-dimethylaminoanthraquinone,
2,3-dimethylanthraquinone,
2-tert-butylanthraquinone,
1-chloroanthraquinone,
2-chloroanthraquinone,
1,5-dichloroanthraquinone,
1,2-dimethoxyanthraquinone,
1,2-diacetoxy-anthraquinone,
5,12-naphthacenequinone,
6,13-pentacenequinone,
xanthone,
thioxanthone,
2,4-dimethylthioxanthone,
2,4-diethylthioxanthone,
2-chlorothioxanthone,
9 (10H)-acridone,
9-methyl-9 (10H)-acridone, and
dibenzosuberenone.

α-Diketone Compounds:
camphorquinone,
benzyl,
diacetyl,
acetylbenzoyl,
2,3-pentadion,
2,3-octadion,
4,4'-dimethoxybenzyl,
4,4'-oxybenzyl,
9,10-phenanthrenequinone, and
acenaphthenequinone.

Ketocumarin Compounds:
3-benzoyl coumarin,
3-(4-methoxybenzoyl) coumarin,
3-benzoyl-7-methoxy coumarin,
3-(4-methoxybenzoyl)7-methoxy-3-coumarin,
3-acetyl-7-dimethylaminocoumarin,
3-benzoyl-7-dimethylaminocoumarin,
3,3'-cumarinoketone, and
3,3'-bis(7-diethylaminocoumarino)ketone.

These oxidizable photo radical generators can be used alone or being mixed together in two or more kinds. It is desired that the amount of use thereof is, usually, 0.001 to 20 mols and, particularly, 0.005 to 10 mols per mole of the photo acid generator though it may vary depending upon the other components used in combination and the kind of the polymerizable monomers (II).

Cationically Polymerizable Monomers (II)

In the present invention, an oxetane compound and an epoxy compound or an alkenyl ether compound are used in combination as cationically polymerizable monomers (II).

Oxetane Compound

The oxetane compound contains at least one oxetane functional group (group having an oxetane ring which is a four-membered cyclic ether) in the molecule, and is a four-membered cyclic (oxetane ring) ether represented, for example, by the following formula (1),

(1)

wherein m is an integer of 0 to 6, $R^1$ is a monovalent group and when m is 2 to 6, a plurality of the groups $R^1$ may be the same or different and, besides, the plurality of the groups $R^1$ may be bonded together to form a ring.

There is no particular limitation on the oxetane compound used in the present invention provided it has an oxetane functional group that can be cationically polymerized, and any known compound can be used. It is, however, desired to use a compound in which one or two groups $R^1$ in the above formula (1) are bonded to the third position of the oxetane ring, but no group $R^1$ is bonded to other positions. The oxetane compound may have one oxetane functional group (i.e., may have one oxetane ring) or may have two or more oxetane functional groups. Concrete examples thereof are as described below.

Compounds Having One Oxetane Functional Group:
3-methyl-3-oxetanylmethanol,
3-ethyl-3-oxetanylmethanol,
3-ethyl-3-phenoxymethyloxetane,
3,3-diethyloxetane, and 3-ethyl-3-(2-ethylhexyloxy)methyloxetane.

Compounds Having Two or More Oxetane Functional Groups:
1,4-bis(3-ethyl-3-oxetanylmethyloxy)benzene,
4,4'-bis(3-ethyl-3-oxetanylmethyloxy)biphenyl,
4,4'-bis(3-ethyl-3-oxetanylmethyloxymethyl)biphenyl,
ethylene glycol bis(3-ethyl-3-oxetanylmethyl)ether,
bis(3-ethyl-3-oxetanylmethyl)diphenoate,
trimethylolpropanetris(3-ethyl-3-oxetanylmethyl)ether,
pentaerythritoltetrakis(3-ethyl-3-oxetanylmethyl)ether,
1,3-bis[(3-ethyloxycetane-3-yl)methoxy]benzene,
2,2'-bis[(3-ethyloxycetane-3-yl)methoxy]biphenyl,
bis[4-(3-ethyloxycetane-3-yl)methoxyphenyl]methane,
bis[2-(3-ethyloxycetane-3-yl)methoxyphenyl]methane,
[2-(3-ethyloxycetane-3-yl)methoxyphenyl][4-(3-ethyloxycetane-3-yl)methoxyphenyl]methane, and
compounds represented by the following formulas:

These oxetane compounds may be used alone or may be used in a combination of a plurality of kinds. Among these oxetane compounds, further, it is desired to use the one having two or more oxetane functional groups in molecules from the standpoint of properties of the cured body that is obtained.

Epoxy Compound

The epoxy compound used in combination with the above oxetane compound has at least one epoxy functional group in the molecule thereof, and is expressed, for example, by the following formula (2),

(2)

wherein n is an integer of 0 to 4, $R^2$ is a monovalent group and when n is 2 to 4, a plurality of the groups $R^2$ may be the same or different and, besides, the plurality of the groups $R^2$ may be bonded together to form a ring.

There is no particular limitation on the epoxy compound provided it can be cationically polymerized, and any known compound can be used. In the above formula (2), however, it is desired that 1 to 3 groups $R^2$ are bonded to the epoxy

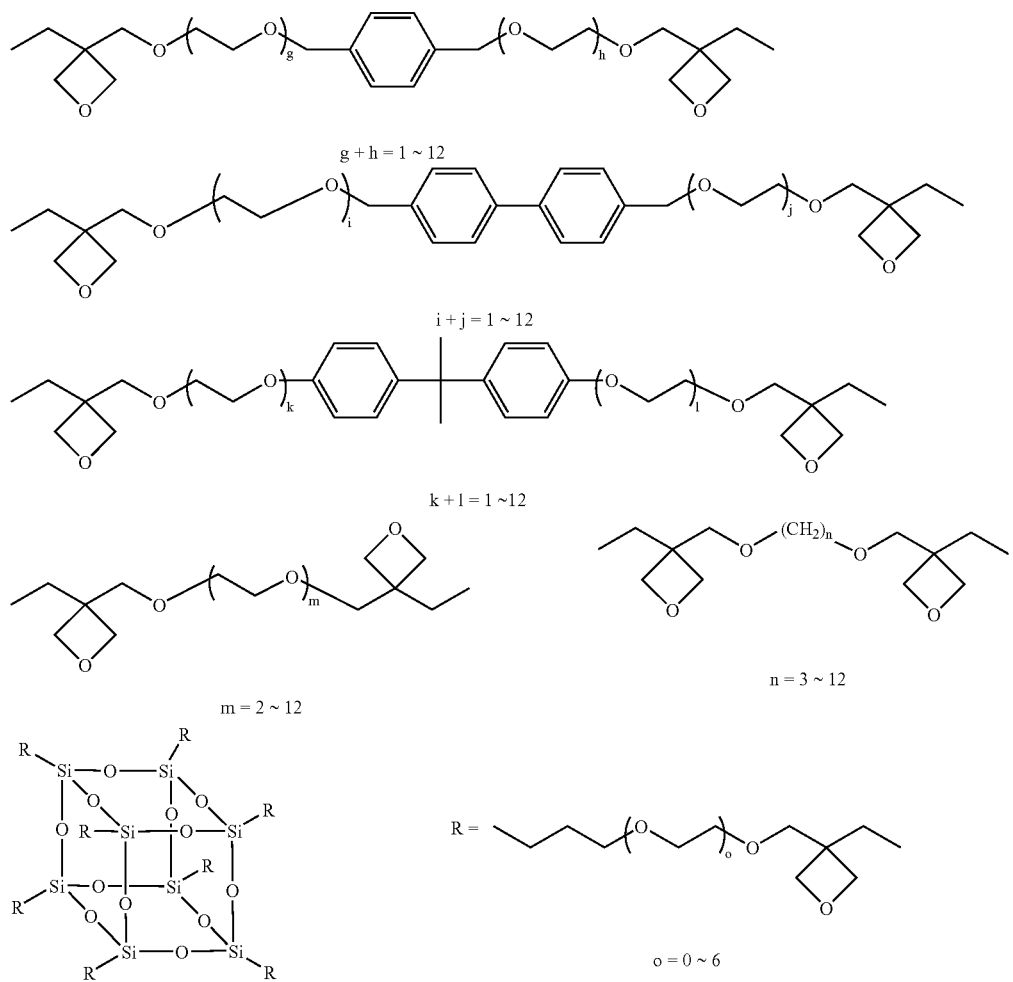

ring. The epoxy compound may have one epoxy functional group in the molecules (i.e., may have one epoxy ring), may have two epoxy functional groups, or may have three or more epoxy functional groups. Concrete examples thereof are as described below.

Compounds Having One Epoxy Functional Group:
1,2-epoxypropane,
1,2-epoxybutane,
1,2-epoxypentane,
2,3-epoxypentane,
1,2-epoxyhexane,
1,2-epoxyoctane,
1,2-epoxydecane,
1,2-epoxydodecane,
1,2-epoxytetradecane,
1,2-epoxyhexadecane,
1,2-epoxyoctadecane,
butadiene monoxide,
2-methyl-2-vinyloxysilane,
1,2-epoxy-5-hexene,
1,2-epoxy-7-octene,
1,2-epoxy-9-decene,
epichlorohydrin,
epibromohydrin,
glycidol,
2-methylglycidol,
methylglycidyl ether,
ethylglycidyl ether,
glycidylpropyl ether,
butylglycidyl ether,
2-ethylhexylglycidyl ether,
cyclooctene oxide,
cyclohexene oxide,
cyclooctene oxide,
cyclododecane epoxide,
exo-2,3-epoxynorbornene,
4-vinyl-1-cyclohexene-1,2-epoxide,
limonene oxide,
styrene oxide,
(2,3-epoxypropyl)benzene,
phenylglycidyl ether,
benzylglycidyl ether,
glycidyl 2-methylphenyl ether,
4-tert-butylphenylglycidyl ether,
4-chlorophenylglycidyl ether, and
glycidyl 4-methoxyphenyl ether.

Compounds Having Two Epoxy Functional Groups:
1,3-butadiene dioxide,
1,2,7,8-diepoxyoctane,
ethylene glycol diglycidyl ether,
diethylene glycol diglycidyl ether,
triethylene glycol diglycidyl ether,
tetraethylene glycol diglycidyl ether,
neopentyl glycol diglycidyl ether,
1,3-propanedioldiglycidyl ether,
1,4-butanedioldiglycidyl ether,
1,5-pentanedioldiglycidyl ether,
1,6-hexanedioldiglycidyl ether,
1,4-cyclohexanemethanoldiglycidyl ether,
diglycidyl glutarate,
diglycidyl adipate,
diglycidyl pimelate,
diglycidyl suberate,
diglycidyl azerate,
diglycidyl sebacate,
2,2-bis[4-glycidyloxyphenyl]propane,
2,2-bis[4-glycidyloxyphenyl]hexafluoropropane,
4-vinyl-1-cyclohexene diepoxide,
limonene diepoxide,
1,2,5,6-diepoxycyclooctane,
3,4-epoxycyclohexylmethyl-3,4-epoxycyclohexane carboxylate,
bis(3,4-epoxycyclohexylmethyl)glutarate,
bis(3,4-epoxycyclohexylmethyl)adipate,
bis(3,4-epoxycyclohexylmethyl)pimelate,
bis(3,4-epoxycyclohexylmethyl)suberate,
bis(3,4-epoxycyclohexylmethyl)azerate,
bis(3,4-epoxycyclohexylmethyl)sebacate,
1,4-bis(3,4-epoxycyclohexylmethyloxymethyl)benzene,
4,4-bis(3,4-epoxycyclohexylmethyloxymethyl)biphenyl,
2,2-bis(3,4-epoxycyclohexyl)propane,
bis(3,4-epoxycyclohexyl),
methylbis[2-(7-oxabicyclo[4.1.0]hepto-3-yl)ethyl] phenylsilane,
dimethylbis[(7-oxabicyclo[4.1.0]hepto-3-yl)methyl]silane,
methyl[(7-oxabicyclo[4.1.0]hepto-3-il)methyl][2-(7-oxabicyclo[4.1.0]hepto-3-yl)ethyl]silane,
1,4-phenylenebis[dimethyl[2-(7-oxabicyclo[4.1.0]hepto-3-yl)ethyl]]silane,
1,2-ethylenebis[dimethyl[2-(7-oxabicyclo[4.1.0]hepto-3-yl)ethyl]]silane,
dimethyl[2-(7-oxabicyclo[4.1.0]hepto-3-yl)ethyl]silane,
1,3-bis[2-(7-oxabicyclo[4.1.0]hepto-3-yl)ethyl]-1,1,3,3-tetramethyldisiloxane,
2,5-bicyclo[2.2.1]heptylenebis[dimethyl[2-(7-oxabicyclo[4.1.0]hepto-3-yl)ethyl]]silane, and
1,6-hexylenebis[dimethyl[2-(7-oxabicyclo[4.1.0]hepto-3-yl)ethyl]]silane.

Compounds Having Three or More Epoxy Functional Groups:
glyceroltriglycidyl ether,
trimethylolpropanetriglycidyl ether,
pentaerythritoltriglycidyl ether,
pentaerythritoltetraglycidyl ether,
dipentaerythritolhexaglycidyl ether, and compounds represented by the following formulas:

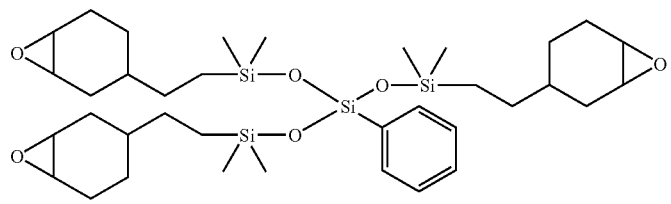

-continued

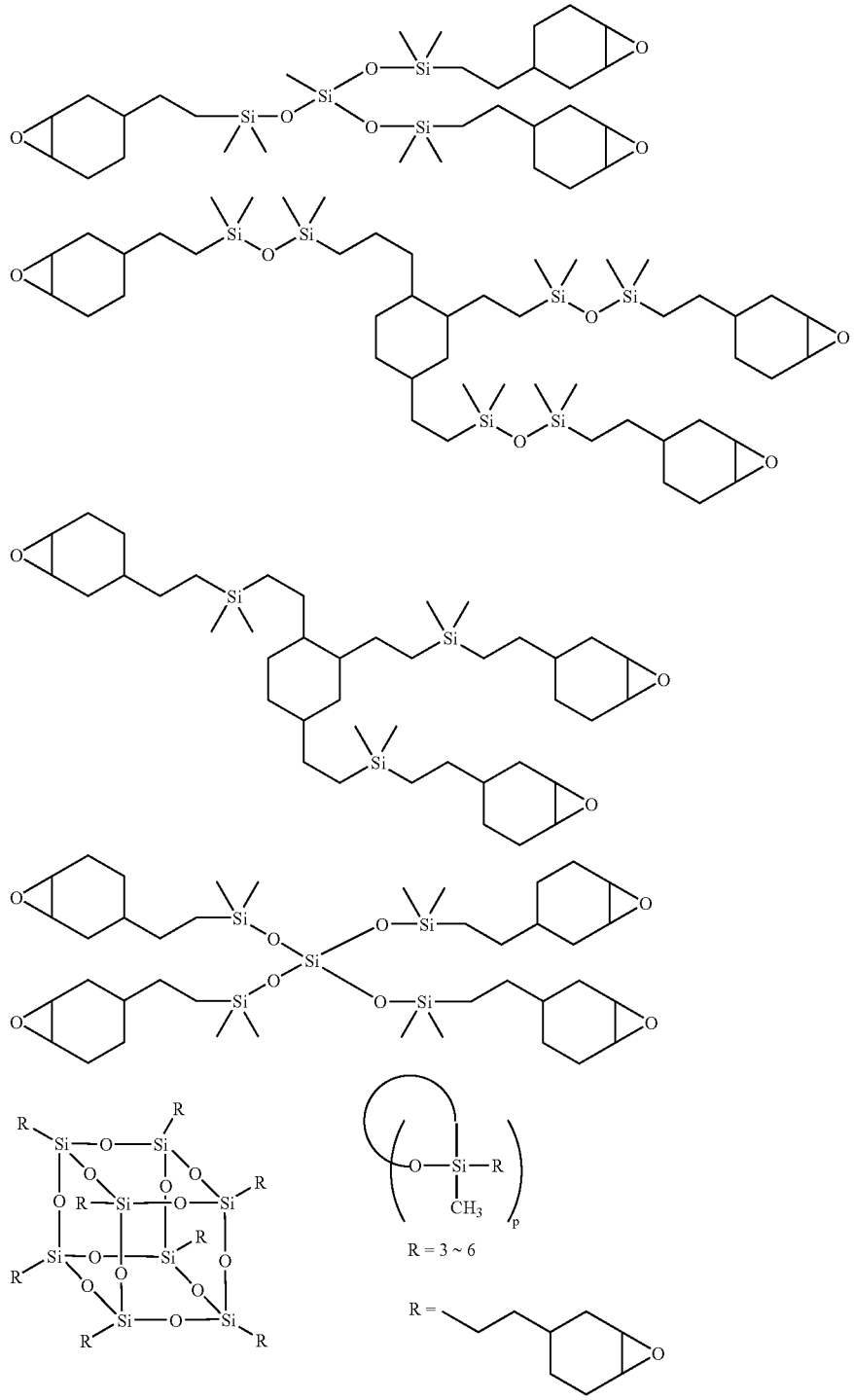

The above epoxy compounds may be used alone or in a combination of a plurality of kinds. In the present invention, it is desired to use the epoxy compound having two or more epoxy functional groups in the molecules from the standpoint of properties of the cured body that is obtained.

Alkenyl Ether Compound

In the present invention, it is allowable to use an alkenyl ether compound instead of the above-mentioned epoxy compound in combination with the oxetane compound. The alkenyl ether compound has at least one alkenyl ether functional group (i.e., a group having a structure $>C=C-O-R$) in the molecule, and is represented by, for example, the following formula (3), $$(R^4)_2C=C(OR^3)(R^4) \qquad (3)$$

wherein $R^3$ is an alkyl group that may have a substituent, and $R^4$ is a hydrogen atom or a monovalent group, and a plurality of $R^4$ may be different from each other.

There is no particular limitation on the alkenyl ether compound provided it can be cationically polymerized, and any known compound can be used. Generally, however, it is desired to use a compound in which $R^4$ in the above formula (3) is a hydrogen atom or an alkyl group. From the standpoint of easy availability, further, it is desired to use a compound (vinyl ether compound) in which a plurality of $R^4$ are all hydrogen atoms.

A representative alkenyl ether compound that can be used in the present invention may have one alkenyl ether functional group, may have two alkenyl ether functional groups or may have three or more alkenyl ether functional groups. Concrete examples thereof are as described below.

Compounds Having One Alkenyl Ether Functional Group:
methyl vinyl ether,
ethyl vinyl ether,
propyl vinyl ether,
butyl vinyl ether,
isobutyl vinyl ether,
t-butyl vinyl ether,
2-ethylhexyl vinyl ether,
dodecyl vinyl ether,
2-chloroethyl vinyl ether,
4-hydroxybutyl vinyl ether,
cyclohexyl vinyl ether,
glycidyl vinyl ether,
1,4-cyclohexanedimethanol monovinyl ether,
ethylene glycol methyl vinyl ether,
triethylene glycol methyl vinyl ether,
ethylene glycol monovinyl ether,
ethylene glycol phenyl vinyl ether,
ethyl-1-propenyl ether,
hexyl-1-propenyl ether,
2-ethylhexyl-1-propenyl ether,
1-methoxy-1,3-butanediene, and
2-(1-propenyloxymethyl)-1,3-dioxolan-2-one.

Compounds Having Two Alkenyl Ether Functional Groups:
Compounds represented by the following formulas:

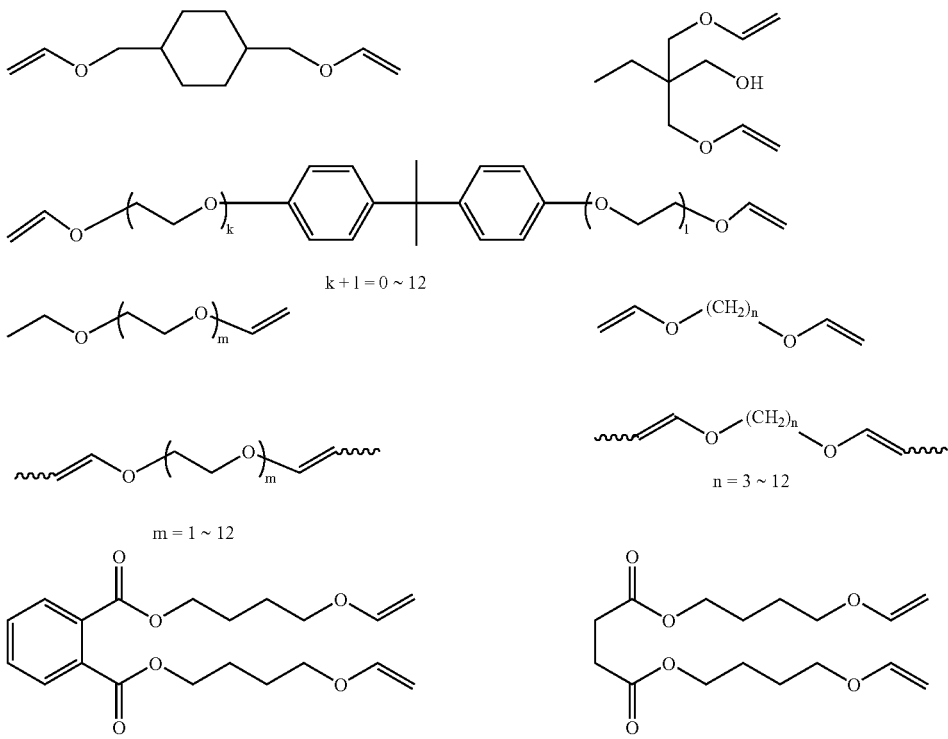

Compounds Having Three or More Alkenyl Ether Functional Groups:
Compounds represented by the following formulas:

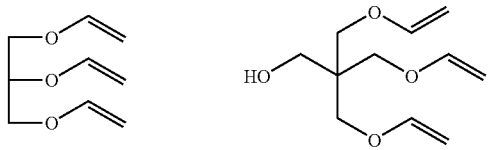

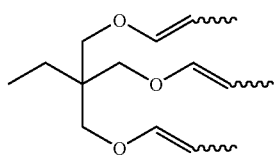

-continued

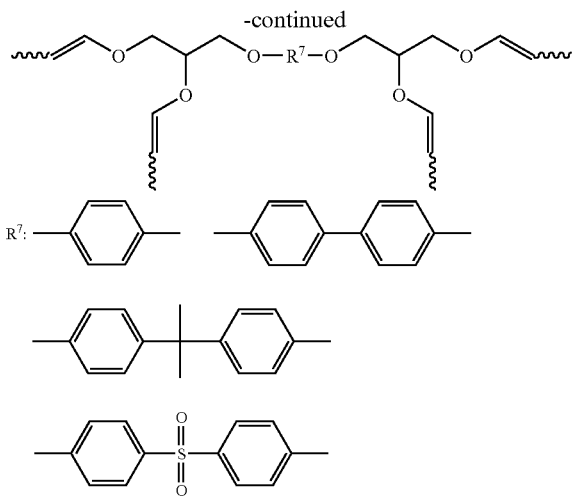

The above alkenyl ether compounds may be used alone or in a combination of a plurality of kinds thereof.

Composition of the Polymerizable Monomers (II)

In the present invention, the greatest feature resides in that the above-mentioned oxetane compound and the epoxy compound or the alkenyl ether compounds are used at such a ratio of amounts that a ratio of the oxetane functional groups and the epoxy functional groups or the alkenyl ether functional groups lies within a particular range. These compounds are used at a ratio of amounts that satisfies the conditions expressed by the following formula, $(a \times A):(b \times B)=91:9$ to $45:55$ wherein A is a mol number of the oxetane compound, a is an average number of the oxetane functional group contained in one molecule of the oxetane compound, B is a mol number of the epoxy compound or the alkenyl ether compound, and b is an average number of the epoxy functional group contained in one molecule of the epoxy compound or an average number of the alkenyl ether functional group contained in one molecule of the alkenyl ether compound.

As will be understood from the above formula, the oxetane compound and the epoxy compound or the alkyl ether compound are used in combination such that a total number of the oxetane functional groups and a total number of the epoxy functional groups or the alkenyl ether functional groups lie in the above-mentioned range, whereby the contraction due to the polymerization greatly decreases, the polymerization is avoided from being hindered by oxygen or water, and the composition can be used even under a highly humid condition such as in the oral cavity. Further, a quick curing can be accomplished, and a cured product is obtained suppressing a change in the color tone before and after the curing and exhibiting excellent aesthetic appearance.

In the above formula, the average numbers a and b of the functional groups are calculated as described below.

For example, when one kind of the oxetane compound is used, an average number a of the oxetane functional groups represents the number of the oxetane functional groups which the one kind of the oxetane compound possesses in one molecule thereof. Even when a plurality of kinds of the oxetane compounds are used, an average number a of the oxetane functional groups represents the number of the oxetane functional groups which is possessed by each of the oxetane compounds in one molecule thereof provided the oxetane compounds have the same number of the oxetane functional groups in one molecule thereof.

In using the plurality of the oxetane compounds, on the other hand, when the number of the oxetane functional groups included in one molecule is different depending upon the oxetane compounds, an average number a of the oxetane functional groups is calculated depending upon the mol ratio of the oxetane compounds that are used. For example, when an oxetane compound having only one oxetane functional group and an oxetane compound having two oxetane functional groups are used in an equimolar amount, an average number a becomes 1.5, and the ratio of amounts of the left side of the above formula may be calculated by using this value. Similarly, when the oxetane compound having only one oxetane functional group and the oxetane compound having two oxetane functional groups are used at a molar ratio of 1:3, an average number a becomes 1.75, and the ratio of amounts of the left side of the above formula may be calculated by using this value.

Average numbers b of the functional group per one molecule of the epoxy compound and of the alkenyl ether compound may be calculated in the same manner as described above.

In the present invention, further, the oxetane compound, epoxy compound and alkenyl ether compound all have, necessarily, one or more functional groups and, hence, neither a nor b becomes smaller than 1. From the standpoint of easy availability of the compounds, handling property such as viscosity of the curable composition of the present invention and mechanical properties of the cured product, it is desired that both a and b are in a range of 1 to 10 and, particularly, 1.5 to 6.

Further, when the epoxy compound and the alkenyl ether compound are used in combination, the value (b×B) of the above formula may be calculated for each of them, and the ratio of amounts of the above formula may be calculated based on the total value thereof.

In the present invention, when the oxetane compound and the epoxy compound are used in combination, the ratio of the functional groups [(a×A):(b×B)] represented by the above formula is preferably in a range of 80:20 to 45:55 and, more preferably, in a range of 80:20 to 55:45. When the oxetane compound and the alkenyl ether compound are used in combination, further, the ratio of the functional groups is preferably in a range of 85:15 to 50:50 and, more preferably, in a range of 85:15 to 55:45.

In the present invention, so far as the ratio of the functional groups [(a×A):(b×B)] satisfies the above-mentioned formula, it is allowed to use in combination any compound having other cationically polymerizable functional groups. As the ratio of the other cationically polymerizable functional groups increases in the cationically polymerizable functional groups in the curable composition, however, the rate of curing decreases and the coloring becomes conspicuous. Therefore, when the sum of the whole cationically polymerizable functional groups in The cationically curable composition is presumed to be 100 mol %, it is desired that the ratio occupied by other functional groups is smaller than 30 mol %, preferably, smaller than 10 mol %, and more preferably, smaller than 5 mol %. Most preferably, there does not substantially exist other cationically polymerizable functional group except the oxetane functional groups, epoxy functional groups and alkenyl ether functional groups.

Other Components

Polymerizable Monomers of Other Types

The curable composition of the present invention may, as required, be blended with an addition polymerization-type radically polymerizable monomer such as a (meth)acrylate monomer in addition to the above-mentioned cationically polymerizable monomers. Upon being blended with the addition polymerization-type radically polymerizable monomer, the apparent curing time can be further shortened. However, the addition polymerization-type radically polymerizable monomer is hindered by oxygen from being polymerized. It is not therefore desired to use the addition polymerization-type radically polymerizable monomer in too large amounts. When the radically polymerizable monomer is to be blended, it is desired that the blending amount thereof is not larger than 30 mass % and, particularly, not larger than 10 mass % per 100 mass % of the total of the cationically polymerizable monomer and the radically polymerizable monomer.

Concrete examples of the addition polymerization-type radically polymerizable monomer include the following (meth)acrylate monomers.
methyl(meth)acrylate,
polyethylene glycol mono(meth)acrylate,
allyl(meth)acrylate,
2-hydroxyethylmono(meth)acrylate,
ethylene glycol di(meth)acrylate,
diethylene glycol di(meth)acrylate,
triethylene glycol di(meth)acrylate,
nonaethylene glycol di(meth)acrylate,
propylene glycol di(meth)acrylate,
dipropylene glycol di(meth)acrylate,
2,2-bis[4-(meth)acryloyloxyethoxyphenyl]propane,
2,2-bis[4-(meth)acryloyloxyethoxyethoxyphenyl]propane,
2,2-bis{4-[2-hydroxy-3-(meth)acryloyloxypropoxy] phenyl}propane,
1,4-butanediol di(meth)acrylate,
1,3-hexanediol di(meth)acrylate,
urethane di(meth)acrylate, and trimethylolpropane di(meth) acrylate.

When the above-mentioned (meta)acrylate monomers are used, it is desired that the oxetane compound, the epoxy compound or the alkenyl ether compound has a radical polymerizable group which can copolymerize with the (meta)acrylate monomers.

Filler (III)

It is desired that the cationically curable composition for dental use of the present invention is blended with a filler in addition to being blended with the polymerization initiator (I) and the cationically polymerizable monomers (II) to further decrease the contraction when it is polymerized. Use of the filler makes it possible to improve the operation property of the curable composition before being cured, or to improve the mechanical properties of the cured product enabling the filler/restorative material for dental use to be highly utilizable.

The kind of the filler and the blending amount thereof may be suitably set depending upon the use of the composition. For example, when the cationically curable composition for dental use of the present invention is used as a filling/restorative material, it is generally desired that the filler is blended in an amount of 50 to 1500 parts by mass and, particularly, 70 to 1000 parts by mass per 100 parts by mass of the above-mentioned cationically polymerizable monomers (II). As the filler for the filling/restorative material for dental use, there can be preferably used inorganic oxides such as amorphous silica, silica-titania, silica-zirconia, silica-titania-barium oxide, quartz and alumina. Further, the inorganic oxides may contain small amounts of metal oxides of the Group I of periodic table in order to obtain dense particles upon the firing at a high temperature. Particles of such a mixed oxide can also be used as a filler. For the dental use, in particular, an inorganic filler of a mixed oxide containing silica and zirconia as chief constituent components is particularly preferred owing to its X-ray contrast property.

There is no particular limitation on the particle size and shape of the inorganic filler. For example, the particles may have a shape (e.g., spherical shape, irregular shape) that is usually assumed by the materials for dental use, and the particles having an average particle size of 0.01 µm to 100 µm may be suitably used depending upon the object. There is no particular limitation, either, on the refractive index of the fillers, and those having a refractive index over a range of 1.4 to 1.7 can be used without limitation as generally possessed by the fillers for dental compositions. Among them, it is desired to use an inorganic powder and/or an aggregate thereof having a spherical shape or a nearly spherical shape to obtain high surface luster and abrasion resistance. The nearly spherical shape referred to here stands for that of an inorganic filler having an average degree of symmetry of not smaller than 0.6 as photographed by using a scanning electron microscope and as found by dividing, by a maximum size thereof, a particle size in a direction at right angles with the maximum size of the particles observed in a unit visual field. To obtain higher surface luster and abrasion resistance, in particular, it is desired to use inorganic particles having an average particle size of 0.01 µm to 1 µm and/or an inorganic spherical filler comprising aggregates of the inorganic particles.

In the present invention, it is desired that the above inorganic fillers are treated with a surface-treating agent as represented by a silane coupling agent to improve affinity to the polymerizable monomers and to improve mechanical strength and resistance to water. The surface treatment can be conducted by a known method. As the silane coupling agent, there can be used methyltrimethoxysilane, methyltriethoxysilane, methyltrichlorosilane, dimethyldichlorosilane, trimethylchlorosilane, vinyltrimethoxysilane, vinyltriethoxysilane, vinyltrichlorosilane, vinyltriacetoxysilane, vinyltris (2-methoxyethoxy)silane, 3-methacryloyloxypropyltrimethoxysilane, 3-methacryloyloxypropyltris(2-methoxyethoxy)silane, 3-chloropropyltrimethoxysilane, 3-chloropropylmethyldimethoxysilane, 3-glycidyloxypropyltrimethoxysilane, 3-glycidyloxypropylmethyldiethoxysilane, 2-(3,4-epoxycyclohexyl)ethyltrimethoxysilane, 5,6-epoxyhexyltriethoxysilane, and 3-ethyl-3-[3-(triethoxysilyl)propoxymethyl]oxetane. From the standpoint of accomplishing good affinity to the cationically polymerizable monomers, in particular, it is desired to use a silane coupling agent having a cationically polymerizable functional group, such as 3-glycidyloxypropyltrimethoxysilane, 3-glycidyloxypropylmethyldiethoxysilane, 2-(3,4-epoxycyclohexyl)ethyltrimethoxysilane, 5,6-epoxyhexyltriethoxysilane, and 3-ethyl-3-[3-(triethoxysilyl)propoxymethyl]oxetane. The above silane coupling agents may be used in one kind or in a combination of two or more kinds.

In the present invention, further, when silica mixed oxides are used, such as silica-titania and silica-zirconia as inorganic fillers, there occurs a problem in that the composition is cured while being preserved for extended periods of time since these mixed oxides have a strong acidity on the surfaces thereof. To improve this problem, the silica mixed oxides may be treated by using the above silane coupling agent in combination with a silane coupling agent that contains nitrogen atoms. In the coupling agent containing nitrogen atoms, there is no limitation in a form in which nitrogen atoms exist; i.e., nitrogen atoms may exist in any form, such as amino group, heterocyclic group containing nitrogen atoms in a ring, amide group, imide group, urethane (carbamate) group, urea group, cyano group, isocyanate group and ammonium group. Among them, it is desired to the one having an amino group, an urethane group, an urea group or an ammonium group as the group containing the nitrogen atom, from the standpoint of easy availability. Concrete examples of such silane coupling agent include 4-aminobutyltrimethoxysilane, N-(2-aminoethyl)-3-aminopropyltrimethoxysilane, N-(2-aminoethyl)-3-aminopropylmethyldimethoxysilane, N-(6-aminohexyl)-3-aminopropyltrimethoxysilane, bis(2-hydroxyethyl)-3-aminopropyltriethoxysilane, N-(hydroxyethyl)-N-methylaminopropyltrimethoxysilane, (3-trimethoxysilylpropyl)diethylenetriamine, N-methylaminopropyltrimethoxysilane, (N,N-dimethylaminopropyl)trimethoxysilane, 3-dimethylaminopropyltrimethoxysilane, 3-dimethylaminopropylmethyldimethoxysilane, 3-(N-allylamino)propyltrimethoxysilane, (aminoethylaminomethyl)phenetyltrimethoxysilane, 3-(m-aminophenoxy)propyltrimethoxysilane, m-aminophenyltrimethoxysilane, p-aminophenyltrimethoxysilane, bis(methyldiethoxysilylpropyl)amine, bis(trimethoxysilylpropyl)amine, bis[3-(trimethoxysilyl)propyl]ethylenediamine, 3-aminopropylmethyldimethoxysilane, 3-aminopropylmethyldiethoxysilane, 3-aminopropyltrimethoxysilane, 3-aminopropyltriethoxysilane, N-(3-methacryloxy-2-hydroxypropyl)-3-aminopropyltriethoxy silane, bis[3-(triethoxysilyl)propyl]urea, N-1-phenetylethyl-N'-triethoxysilylpropylurea, O-(vinyloxyethyl)-N-(triethoxysilylpropyl)urethane, O-(methacryloxyethyl)-N-(triethoxypropyl)urethane, O-(propargyloxy)-N-(triethoxysilylpropyl)urethane, (3-triethoxysilylpropyl)-t-butyl carbamate, triethoxysilylpropylethyl carbamate, N-triethoxysilylpropyl-O-menthocarbamate, N-(triethoxysilylpropyl)-O-polyethylene oxide urethane, N,N-didecyl-N-methyl-N-(3-trimethoxysilylpropyl)ammonium chloride, octadecyldimethyl(3-trimethoxysilylpropyl)ammonium chloride, 3-(N-styrylmethyl-2-aminoethylamino)propyltrimethoxysilane hydrochloride, tetradecylmethyl(3-trimethoxysilylpropyl)ammonium chloride, N-(trimethoxysilylethyl)benzyl-N,N,N-trimethylammonium chloride, N-(trimethylsilylpropyl)isothiolonium chloride, N-trimethoxysilylethyl-N,N,N-tributylammonium bromide, N-trimethoxysilylethyl-N,N,N-tributylammonium chloride and N-trimethoxysilylethyl-N,N,N-trimethylammonium chloride.

The silane coupling agents containing these nitrogen atoms may be used in a plurality of kinds in combination.

When the specific surface area of the silica mixed oxide is denoted by X m$^2$/g, the amount of the silane coupling agent containing nitrogen atoms by C mmol and the amount of the silane coupling agent without nitrogen atom by D mmol, the silane coupling agent containing nitrogen atoms and other silane coupling agents without nitrogen atom may be used at such a ratio that (C+D)/X is 0.007 to 0.03 per gram of the composite oxide and A:B is 0.01:99.99 to 30:70.

The invention may, further, suitably use an organic/inorganic composite filler to accomplish both a high affinity to the polymerizable monomer and a favorable operation property. The organic/inorganic composite filler is obtained by polymerizing and curing the polymerizable and curable composition comprising chiefly polymerizable monomers and inorganic fillers, followed by milling. According to the present invention, there can be used any organic/inorganic composite filler produced by a known production method without limitation.

The organic/inorganic composite filler is produced in a manner as described below.

For example, the polymerizable monomer that can be used as a starting material for producing the organic/inorganic composite filler may be any one of the addition polymerization type, ring-opening polymerization type, polycondensation type or polyaddition type. Among them, monomers of the addition polymerization type and, particularly, (meth)acrylates are preferred since they form no by-product, and there is no need of adjusting the equivalents of the functional groups of the two kinds of monomers. Representative examples are a (meth)acrylate monomer (hereinafter referred to as monofunctional (meth)acrylate) having one (meth)acryloxy group as a polymerizable unsaturated group and a (meth)acrylate monomer (hereinafter referred to as polyfunctional (meth)acrylate) having a plurality of (meth)acryloxy groups as polymerizable unsaturated groups. Concrete examples are as described below.

Monofunctional (meth)acrylates:
methyl(meth)acrylate,
ethyl(meth)acrylate,
isopropyl(meth)acrylate,
butyl(meth)acrylate,
2-ethylhexyl(meth)acrylate,
benzyl(meth)acrylate,
2-(meth)acryloyloxyethyl propionate,
2-methacryloxyethyl acetoacetate,
2-methacryloxyethyl acetoacetylacetonato, and (ally (meth)acrylate.

Polyfunctional (meth)acrylates:
ethylene glycol di(meth)acrylate,
diethylene glycol di(meth)acrylate,
triethylene glycol di(meth)acrylate,
butylene glycol di(meth)acrylate,
nonaethylene glycol di(meth)acrylate,
polyethylene glycol di(meth)acrylate,
propylene glycol di(meth)acrylate,
dipropylene glycol di(meth)acrylate,
neopentyl glycol di(meth)acrylate,
1,3-butanediol di(meth)acrylate,
1,3-hexanediol di(meth)acrylate,
1,4-butanediol di(meth)acrylate,
1,5-pentanediol di(meth)acrylate,
1,6-hexanediol di(meth)acrylate,
1,7-heptanediol di(meth)acrylate,
1,8-octanediol di(meth)acrylate,
1,9-nonanediol di(meth)acrylate,
1,10-decanediol di(meth)acrylate,
neopentyl glycol di(meth)acrylate,
trimethylolmethane tri(meth)acrylate,
trimethylolethane tri(meth)acrylate,
trimethylolpropane tri(meth)acrylate,
pentaerythritol tetra(meth)acrylate,
urethane (meth)acrylate,
2,2-bis((meth)acryloyloxyphenyl)propane,
2,2-bis(4-(meth)acryloyloxyethoxyphenyl)propane,
2,2-bis(4-(meth)acryloyloxyethoxyethoxyphenyl)propane, and
2,2-bis(4-(meth)acryloyloxypropoxyphenyl)propane.

Among the above (meth)acrylates according to the present invention, a polyfunctional (meth)acrylate is desired from the standpoint of properties of the organic/inorganic composite filler.

From the standpoint of improving adhesion on the interface between the obtained organic/inorganic composite filler and the cationically polymerizable monomers (II), further, it is also allowable to use a (meth)acrylate monomer having a cationically polymerizable functional group (hereinafter called cationically polymerizable (meth)acrylate) or a (meth)acrylate monomer (hereinafter called hydroxy(meth) acrylate) having a hydroxy group that reacts with the cationically polymerizable functional group. As the cationically polymerizable (meth)acrylate and hydroxy(meth)acrylate, there can be exemplified the following compounds.

Cationically Polymerizable (meth)acrylates:
glycidyl(meth)acrylate,
3,4-epoxycyclohexylmethyl(meth)acrylate,
3-methyl-3,4-epoxycyclohexylmethyl(meth)acrylate,
2-vinyloxyethyl(meth)acrylate,
6-vinyloxyhexyl(meth)acrylate,
3-ethyl-3-(meth)acryloxymethyloxetane,
3-ethyl-3-(2-(meth)acryloxyethyloxymethyl)oxetane,
3-ethyl-3-(3-(meth)acryloxypropyloxymethyl)oxetane,
p-(meth)acryloxymethylstyrene,
tetrahydrofurfuryl(meth)acrylate,
2-glycidyloxy-1,3-propanediol di(meth)acrylate,
2-glycidyloxymethyl-1,3-propanediol di(meth)acrylate,
2-glycidyloxymethyl-2-ethyl-1,3-propanediol di(meth)acrylate, and
(2-bisglycidyloxymethyl-1,3-propanediol di(meth)acrylate.

Hydroxy(meth)acrylates:
2-hydroxyethyl(meth)acrylate,
polyethylene glycol mono(meth)acrylate,
3-hydroxypropyl(meth)acrylate,
glyceryl mono(meth)acrylate,
1,4-butanediol mono(meth)acrylate,
1,5-pentanediol mono(meth)acrylate,
1,6-hexanediol mono(meth)acrylate,
trimethylolpropane di(meth)acrylate,
1,7-heptanediol mono(meth)acrylate,
1,8-octanediol mono(meth)acrylate,
1,9-nonanediol mono(meth)acrylate,
1,10-decanediol mono(meth)acrylate,
trimethylolethane di(meth)acrylate,
trimethylolmethane di(meth)acrylate,
pentaerythritol di(meth)acrylate,
pentaerythritol tri(meth)acrylate, and
2,2-bis[4-{2-hydroxy-3-(meth)acryloxy)propoxyphenyl] }propane.

There is no particular limitation on the amount of blending various polymerizable monomers used for the production of the organic/inorganic composite fillers. However, the above-mentioned monofunctional (meth)acrylate tends to lower the properties of the organic/inorganic composite fillers that are produced. It is therefore better to limit the amount of the monofunctional (meth)acrylate that is used to lie in a range of 0.01 to 70 parts by mass, preferably, 0.01 to 50 parts by mass and, more preferably, 0.01 to 30 parts by mass per 100 parts by mass of the sum of the whole (meth)acrylate monomers.

There is no particular limitation on the shape of the inorganic filler used as a starting material for producing the organic/inorganic composite filler. By taking the properties of the obtained cured product (organic/inorganic composite filler) into consideration, however, it is desired that the inorganic filler used as the starting material has the same shape as that of the inorganic filler that is used alone and has, similarly, been treated with the silane coupling agent.

Though there is no particular limitation, it is desired that the amount of the inorganic filler in the organic/inorganic composite filler is 50 to 1900 parts by mass and, particularly, 200 to 1000 parts by mass per 100 parts by mass of the organic component (polymer of the above (meth)acrylate monomer) to obtain a high mechanical strength.

A mixture of the above (meth)acrylate monomer and the inorganic filler can be polymerized and cured by a method of radical polymerization, anionic polymerization or any other polymerization method. Usually, however, the radical polymerization method is preferred.

A variety of methods can be employed for initiating the radical polymerization, such as a method that uses a photo radical polymerization initiator that is capable of generating polymerization initiating species upon the irradiation with visible light rays or infrared rays, a method that uses an initiator composition capable of generating polymerization initiating species by the reaction of two or more kinds of compounds without being irradiated with light, and a method that uses an initiator capable of generating polymerization initiating species by heating. That is, the mixture of the above (meth)acrylate monomer and the inorganic filler is blended with the above polymerization initiator, and is subjected to the radical polymerization under the conditions that meet the kind of the polymerization initiator. The above polymerization initiators may be used alone or, as required, in a combination of two or more kinds. Described below are concrete examples of the polymerization initiators.

Photo Radical Polymerization Initiators:
benzoin alkyl ether such as benzoin methyl ether, benzoin ethyl ether and benzoin isopropyl ether;
benzyl ketal such as benzyl dimethyl ketal and benzyl diethyl ketal;
diarylketone such as benzophenone, anthraquinone and thioxanthone;
α-diketone such as diacetyl, benzyl, camphorquinone and 9,10-phenanthraquinone; and
bisacylphosphine oxides such as bis-(2,6-dichlorobenzoyl)phenylphosphine oxide, bis-(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, and bis(2,4,6-trimethylbenzoyl) phenylphosphine oxide.

(To the photo radical polymerization initiator, there is often added a reducing compound which may be tertiary amines like 2-(dimethylamino)ethyl methacrylate, ethyl 4-dimethylaminobenoate, N-methyldiethanolamine, dimethylaminobenzaldehyde or terephthalaldehyde; a sulfur-containing compound like 2-mercaptobenzoxazole, 1-decanethiol, thiosalcilic acid or thiobenzoic acid; and N-phenylalanine.)

Radical Polymerization Initiators Other than the Photo Radical Polymerization Initiators:
peroxides such as benzoyl peroxide, p-chlorobenzoyl peroxide, tert-butylperoxy-2-ethyl hexanoate, tert-butylperoxy dicarbonate and diisopropylperoxy dicarbonate;
azo compounds such as azobisisobutylonitriles;
boron compounds such as tributylborane, partial oxide of tributylborane, sodium tetraphenylborate, sodium tetrakis(p-fluorophenyl)borate, and triethanolamine salt of tetraphenylboric acid;
barbituric acids such as 5-butylbarbituric acid and 1-benzyl-5-phenylbarbituric acid; and sulfinates such as sodium benzenesulfinate and sodium p-toluenesulfinate.

(The radical polymerization initiator others than the photo radical polymerization initiators may be used in combination with the above-mentioned reducing compounds.)

The amount of addition of the radical polymerization initiator may be selected depending upon the object and is, usually, selected to be 0.01 to 10 parts by mass and, particularly, 0.1 to 5 parts by mass per 100 parts by mass of the (meth)acrylate monomer.

The cured product obtained by polymerizing and curing the mixture of the polymerizable monomers and the inorganic filler is usually milled into particles adjusted to a suitable degree of particle sizes (average particle size of about 0.1 to about 100 μm) and is used as an organic/inorganic composite filler. The cured product may be put to a suitable heat treatment before or after being milled to improve properties.

The milling can be conducted relying upon any known method without limitation. Preferably, the milling is conducted by using a milling machine such as a vibration ball mill or a jet mill. Further, either the wet milling or the dry milling may be employed.

As required, further, the organic/inorganic composite filler obtained as described above is subjected to the surface treatment with the above-mentioned silane coupling agent before being put to the use.

As required, further, the present invention uses an inorganic filler of organic polymer particles in addition to the above-mentioned inorganic filler and the organic/inorganic composite filler. As the organic polymers, there can be exemplified polymethyl methacrylate, polyethyl methacrylate, methyl methacrylate/ethyl methacrylate copolymer, crosslinked polymethyl methacrylate, crosslinked polyethyl methacrylate, ethylene/vinyl acetate copolymer, styrene/butadiene copolymer, acrylonitrile/styrene copolymer and acrylonitrile/butadiene/styrene copolymer.

Any of the above fillers can be used for the curable composition of the invention. From the standpoint of obtaining excellent mechanical properties after cured, however, it is desired to use an inorganic filler alone or it is most desired to use an inorganic filler and an organic/inorganic composite filler in combination.

Various Additives

The cationic curable composition for dental use of the present invention may be blended with stabilizers such as polymerization inhibitor, antioxidant and ultraviolet ray absorber as well as known additives such as dye, antistatic agent, pigment, perfume, organic solvent and viscosity-imparting agent.

When, for example, an iodonium salt-type initiator is used as the polymerization initiator (I), it is desired that the polymerization initiator is blended with hindered phenols and hindered amines as a stabilizer to suppress the gelation of the curable composition under relatively high temperature conditions of about 50° C. or when being preserved for extended periods of time at room temperature.

As the hindered phenols, there can be exemplified:
2,6-di-t-butylphenol,
2,6-di-t-butyl-4-methylphenol,
2,4,6-tri-t-butylphenol,
n-octadecyl-3-(3,5-di-t-butyl-4-hydroxyphenyl) propionate,
tetrakis[methylene-3-(3,5-di-t-butyl-4-hydroxyphenyl)propionate]methane, and
tris(3,5-di-t-butyl-4-hydroxybenzyl)isocyanurate.

These hindered phenols can be used alone or in a combination of two more kinds. The amount of addition thereof is, usually, such that the amount of the hindered phenol groups is 0.001 to 1 mol and, particularly, 0.005 to 0.8 mols per mol of the diaryliodonium salt though it may vary depending upon other components that are used in combination.

Though there is no particular limitation, the hindered amines are preferably those that have been known particularly as photo stabilizers for the resins. Among them, it is desired to use pyrrolidines, piperidines and piperadines which are chemically stable cyclic amines. From the standpoint of easy availability, piperidines are most desired. Concrete examples of the hindered amines are as described below.
2,6-dimethylpiperidine,
N-methyl-2,6-dimethylpiperidine,
N-methyl-2,6-dimethylpiperidine-4-one,
N-methyl-4-hydroxy-2,6-dimethylpiperidine,
2,2,6,6-tetramethylpiperidine,
N-methyl-2,2,6,6-tetramethylpiperidine,
N-methyl-2,2,6,6-tetramethylpiperidine-4-one,
N-methyl-4-hydroxy-2,2,6,6-tetramethylpiperidine,
bis(2,2,6,6-tetramethyl-4-piperidinyl)sebacate,
bis(N-methyl-2,2,6,6-tetramethyl-4-piperidinyl) sebacate,
tetrakis(2,2,6,6-tetramethyl-4-piperidinyl)-1,2,3,4-butane tetracarboxylate,
tetrakis(N-methyl-2,2,6,6-tetramethyl-4-piperidinyl)-1,2,3,4-butane tetracarboxylate,
poly[(6-(1,1,3,3-tetramethylbutyl)imino-1,3,5-triazi/2,4-diyl)][(2,2,6,6-tetramethyl-4-piperidinyl)imino]hexamethylene(2,2,6,6-tetramethyl-4-piperidinyl)iminol, and
polycondensate of dimethyl-1-(2-hydroxyethyl)4-hydroxy-2,2,6,6-tetramethyl-4-piperidine succinate.

These hindered amines can be used alone or in a combination of two or more kinds. The amount of addition thereof may vary depending upon other components used in combination but is, usually, such that the amount of the hindered amino groups is 0.001 to 1 mol and, particularly, 0.005 to 0.8 mols per mol of the diaryliodonium salt from the standpoint of not adversely affecting the properties of the cured product.

Cationically Curable Composition for Dental Use

The cationically curable composition for dental use of the invention containing the above various components can be particularly preferably used as a dental filling/restorative material but can further be used as a dental adhesive, a denture base and in any other applications not being limited thereto only.

Further, there is no particular limitation on the method of producing the curable composition and any known production method may be suitably used. Concretely, the above-mentioned cationic polymerization initiator (I), cationically polymerizable monomers (II) and any other components that are to be blended as required, are weighed in predetermined amounts and are mixed together.

Though there is no particular limitation, the cationically curable composition for dental use of the invention may be suitably packaged by taking the object and preservation stability into consideration. For example, when a photo cationic polymerization initiator is blended as the cationic polymerization initiator (I), the components constituting the curable composition may all be packaged in a manner of shutting off light. Further, when a component which is capable of initiating the cationic polymerization at room temperature without the irradiation with light is used as a polymerization initiator, the components may be divided into two or more separate packages so that they will not be polymerized and cured during the preservation, but may be mixed together just before being used.

As means for curing the dental cationically curable composition of the present invention, there may be employed any known polymerizing means that meets the polymerization initiation mechanism of the cationic polymerization initiator. Concretely, there can be employed without any limitation a method of irradiation with light using a source of light such as of carbon arc, xenon lamp, metal halide lamp, tungsten lamp, fluorescent lamp, sunlight, helium cadmium laser or argon laser, a method of heating by using a heat polymerization unit, or a method based on the combination thereof.

When polymerized by the irradiation with light, the irradiation time differs depending upon the wavelength of the source of light, intensity of light, shape and material of the cured product and may, hence, be determined in advance by conducting preliminary experiment. Generally, however, the ratio of blending the components is so adjusted that the irradiation time lies in a range of about 5 to about 60 seconds. Similarly, the heating time and the heating temperature, too, may be determined in advance through preliminary experiment.

EXAMPLES

The invention will now be concretely described by way of Working Examples which, however, are not to limit the invention. Described below are abbreviations of the compounds used in the specification and in Examples.

1. Oxetane Compounds.

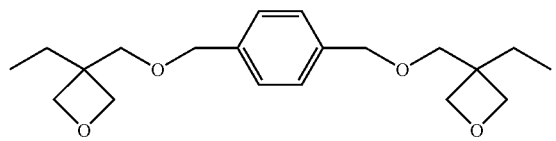

OX-1

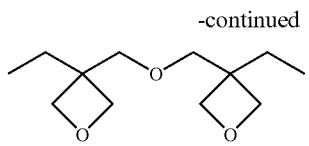

OX-2

2. Epoxy Compounds.

EP-1

EP-2

3. Alkenyl Ether Compounds.

DVE-1

DVE-2

4. Other Cationically Polymerizable Compounds

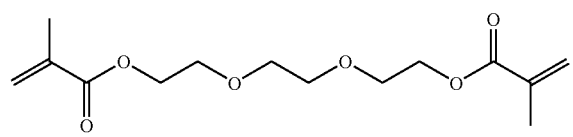

BOE

5. Radically Polymerizable Monomers.

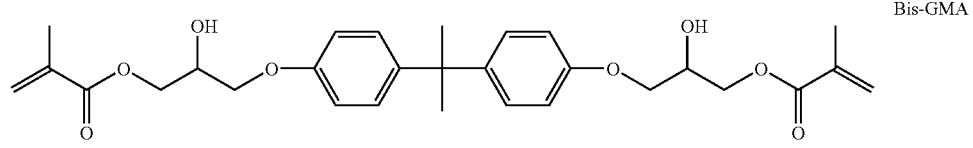

Bis-GMA

3G

6. Photo Acid Generators.

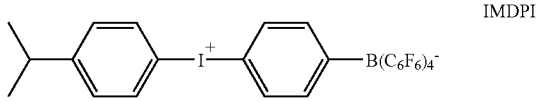

IMDPI

7. Condensed Polycyclic Aromatic Compounds.

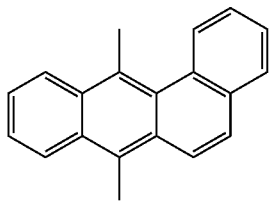

DMBAn

8. Oxidizable Photo Radical Generators
   CQ: Camphorquinone

9. Others.
   DMPT: p-dimethylaminotoluidine
   DMBE: ethyl 4-dimethylaminoethylbenzoate
   APS: 3-aminopropyltrimethoxysilane
   TN765:

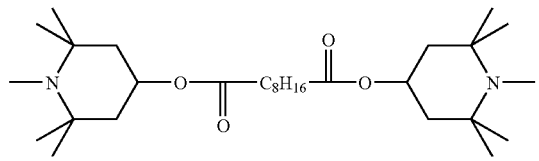

Described below are methods of evaluating the properties in Examples and in Comparative Examples. As for the atmospheric conditions for effecting the curing, the conditions (1) consisted of a temperature of 22° C. and a relative humidity of 20%, and the conditions (2) consisted of a temperature of 37° C. and a relative humidity of 100%. The conditions (2) were set to resemble the environment in an oral cavity.

(1) Surface Condition of the Cured Body.

By using the Pasteur pipette, a curable composition was applied onto the bottom surface of a polytetrafluoroethylene mold having a hole of 6 mm$\phi$×0.3 mm under the conditions (1) or the conditions (2). The curable composition was cured by the irradiation with light by using a dental visible light irradiator (Power Light, Tokuyama Dental Co.) from a distance of about 5 mm over the liquid surface of the composition for 60 seconds. The surface state of the cured body was observed, and whether an unpolymerized portion is existing on the surface was judged on the basis of the following criteria.

X: The irradiated surfaces of the cured product are sticky (unpolymerized portion is existing to a considerable degree on the surfaces).

Δ: The surfaces are not sticky but are whitened (unpolymerized portion is existing to some extent on the surfaces).

○: The surfaces are neither sticky nor whitened (no unpolymerized portion is existing on the surfaces).

(2) Microhardness.

The polytetrafluoroethylene mold having a hole of 6 mm$\phi$×1.5 mm was filled with the curable composition in a manner that the surface thereof was flat under the conditions (1) or the conditions (2). After left to stand in the atmosphere for 3 minutes, the curable composition was covered with a polypropylene film, pressed with a slide glass, and was cured by the irradiation with light from the dental visible light irradiator at a position 5 mm over the filled surface for 60 seconds. After cured, the polypropylene film was peeled off, and irradiated surface was measured for its hardness by using a microhardness tester (MHT-1 manufactured by Matsuzawa Seiki Co.) under a load of 200 g and a loading time of 30 seconds.

(3) Discoloration of the Cured Product.

The polytetrafluoroethylene mold having a hole of 6 mm$\phi$×1.5 mm was filled with the sample curable composition, covered with a polypropylene film, and was measured for its $L^*_0$, $a^*_0$, $b^*_0$ in its uncured state on the black back by using a spectral color-difference meter (Color Analyzer TC-1800MK-II).

Further, the polytetrafluoroethylene mold having a hole of 6 mm$\phi$×1.5 mm was filled with the sample curable composition under the conditions (1), was covered with a polypropylene film, and was pressed with a slide glass. In this state, the curable composition was cured by being irradiated with light from the dental visible light irradiator at a position 5 mm over the filled surface for 60 seconds. After cured, the cured product was taken out from the mold, and was measured for its $L^*_0$, $a^*_0$, $b^*_0$ by using a spectral color-difference meter to calculate a color difference ($\Delta E^*$) before and after the curing in accordance with the following formula, $$\Delta E^* = \{(L^*-L^*_0)^2 + (a^*-a^*_0)^2 + (b^*-b^*_0)^2\}^{1/2}$$

Further, the surface of the cured product was compared with that of the composition of before cured, and the discolored state was observed by naked eyes and was evaluated on the basis of the following criteria.

X: Colored conspicuously as compared with the composition of before cured.

○: Colored to a small degree as compared with the composition of before cured.

⊚: Coloring was not confirmed by naked eyes.

(4) Curing Time of the Composition without Filler.

A polypropylene container of an inner diameter of 1.6 cm and a depth of 1.1 cm was filled with 0.9 g of a sample cationically curable composition such that the thickness of the cured film was 4 mm. The film was irradiated with light by using a dental light irradiator (TOKUSO POWER LITE, manufactured by Tokuyama Co.) form an irradiation distance of 0.5 cm for 2 minutes. Here, the curing time stands for a time from the start of irradiation until when the sharp ends of a pair of tweezers could not be driven into the surface of the cured product despite it was forcibly pushed thereon perpendicularly.

(5) Coefficient of Contraction by Polymerization of the Composition without Filler.

A sample curable composition (liquid composition) before cured was introduced into a 10-ml messflask of which the weight has been known while bringing the liquid level thereof into agreement with an indicator, and was preserved overnight in an incubator maintained at 23° C. After preserved, it was confirmed that the liquid level was in agreement with the indicator, and the weight was measured. The weight of the messflask of before being filled with the composition was subtracted from the measured weight, followed by the division by the volume thereof to calculate the density of the composition. The above operation was conducted using three or more samples, and an average value thereof was regarded to be the density d1 of the composition.

Further, the sample curable composition was introduced into a polypropylene resin container of a diameter of 3 cm and a depth of 1 cm to a depth of 0.5 cm, and was cured by the irradiation with light from a dental light irradiator (α-Light, manufactured by Morita Co.) for 10 minutes. After cured, the composition was left to stand at room temperature for 30 minutes and was measured for its density by using a digital specific gravimeter (manufactured by Zaltorius Co.) and using water (maintained at 23 to 24° C.) as a liquid for generating buoyancy. The same operation was conducted by using three or more samples, and an average value thereof was regarded to be the density d2 of the cured body. From the obtained values d1 and d2, the coefficient of contraction due to polymerization was calculated in compliance with the following formula,

[(d2−d1)/d2]×100=coefficient of contraction (%)

(6) Curing Time of the Composition (Composite Resin) Containing a Filler.

A sample composite resin was piled in a diameter of about 6 mm and a height of 3 mm on a glass plate, and was irradiated with light from a distance of about 5 mm over the upper surface of the pile. By using a needle of a thickness of about 0.4 mm, the upper surface and the side surfaces of the pile were examined for the hardness without interrupting the irradiation of light, and a moment when the needle could not be driven into the pile as a whole was regarded to be the curing time.

(7) Coefficient of Contraction by Polymerization of the Composition (Composite Resin) Containing a Filler.

In an SUS split mold having a hole of a diameter of 3 mm and a height of 7 mm, there was introduced an SUS plunger of a diameter of 3 mm and a height of 4 mm to set the height of the hole to be 3 mm. A sample curable composition was filled therein and a slide glass was pres-contacted thereto from the upper side. The mold was placed with its slide glass surface facing down on a glass plate equipped with a dental irradiator, and a short needle was brought into contact therewith from the upper side of the SUS plunger to measure a very fine motion of the needle. The composition was polymerized and cured by the dental irradiator, and the contraction (%) 10 minutes after the start of irradiation was calculated from the moving distance of the short needle in the up-and-down direction.

(8) Flexural Strength and Flexural Modulus of Elasticity.

A sample curable composition was filled in a metal mold of 2×2×25 mm in an atmosphere of the conditions (1), was covered with a polypropylene film, and was cured by the irradiation with light from a light irradiator for 1.5 minutes. The cured product was preserved overnight at 37° C. By using five cured products, a three-point flexural strength and a flexural modulus of elasticity were measured by using an autograph (manufactured by Shimazu Seisakusho Co.) under the conditions of a distance between fulcrums of 20 mm and a crosshead speed of 0.5 mm/min, and average values thereof were calculated.

(9) Number of Days Before the Composition without Filler was Gelled During the Preservation at 50° C.

The curable composition was preserved in a constant-temperature device maintained at 50° C. under a condition of shutting off the light. The curable composition was taken out from the constant-temperature device every other day, left to cool down to room temperature in a dark place, and was observed for its properties. The composition was compared with the composition comprising the same cationically polymerizable monomer only, and the number of days before the fluidity was greatly lost and the viscosity has increased or before it became like a jelly without fluidity was regarded to be the number of days before gelled.

(10) Number of Days Before the Composition Containing the Filler (Composite Resin) was Gelled During the Preservation at 50° C.

Similarly, the curable composition was preserved in a constant-temperature device maintained at 50° C. under a condition of shutting off the light. The composite resin was taken out from the constant-temperature device every other day, left to cool down to room temperature in a dark place, and was inspected for its properties by using a metallic spatula. The composition was compared with the composition comprising the same cationically polymerizable monomer and the filler only. The composite resin was regarded to be not gelled when the fluidity of the composition has not decreased or when the fluidity has decreased to some extent but when it could not be easily shaped by using the metallic spatula. Whereas, the number of days when the composition has lost the fluidity and could not be shaped by using the metallic spatula, and the composite resin was cracked, or when the composite resin could not be cracked by using the metallic sparula was regarded to be the number of days before gelled.

In the following Examples 1 to 21, the oxetane compound and the epoxy compound were used in combination as cationically polymerizable monomers (II).

Example 1

An oxetane compound (OX-1) and an epoxy compound (EP-1) were blended being so adjusted that the amount of (EP-1) was 0.111 mols per mol of (OX-1) in an environment of a relative humidity of not higher than 20%. In this case, (OX-1) was a bifunctional oxetane compound and, hence, "a" was 2 while (EP-1) was a bifunctional epoxy compound and, hence, "b" was 2, establishing a relationship, (a×A):(b×B)=(2×1):(2×0.111)=90:10

To 100 parts by mass of the mixture of the above polymerizable monomers, there were added 0.1 part by mass of a photo acid generator (IMDPI), 0.03 parts by mass of a condensed polycyclic aromatic compound (DMBAn) and 0.03 parts by mass of camphorquinone (CQ) as polymerization initiators in a dark place. The mixture was stirred and dissolved until it became homogeneous thereby to prepare a curable composition.

The curable composition was evaluated for the curing time, the surface state of the cured product, and the coefficient of contraction by polymerization. The results were as shown in Table 1.

Examples 2 to 4 and Comparative Examples 1 to 7

Curable compositions were prepared in the same manner as in Example 1 but varying the ratio of blending the oxetane compound (OX-1) and the epoxy compound (EP-1) in a manner to accomplish the ratios of functional groups as shown in Table 1, and were evaluated for their properties. The results were as shown in Table 1.

In Table 1, numerals in the column of the exetane compounds represent (a×A) and the numerals in the column of the epoxy compounds represent (b×B) when (a×A)+(b×B) is set to be 100 (the same holds hereinafter in all Tables).

TABLE 1

| | Cationically polymeriable monomer Ratio of functional groups | | Polymerization initiator Parts by mass | | | Surface state of cured product | | Curing time | Contraction by polymerization |
|---|---|---|---|---|---|---|---|---|---|
| | Oxetane compound | Epoxy compound | | | | | | | |
| | OX-1 | EP-1 | IMDPI | DMBAn | CQ | Condition 1 | Condition 2 | (sec) | (%) |
| Comparative Example 1 | 100 | ☐ | 0.1 | 0.03 | 0 | ○ | X | 90 | 3.8 |
| Comparative Example 2 | 95 | 5 | 0.1 | 0.03 | 0 | ○ | X | 60 | 3.8 |
| Comparative Example 3 | 92 | 8 | 0.1 | 0.03 | 0 | ○ | Δ | 33 | 3.8 |
| Example 1 | 90 | 10 | 0.1 | 0.03 | 0 | ○ | ○ | 22 | 3.9 |
| Example 2 | 80 | 20 | 0.1 | 0.03 | 0 | ○ | ○ | 19 | 3.9 |
| Example 3 | 55 | 45 | 0.1 | 0.03 | 0 | ○ | ○ | 16 | 3.9 |
| Example 4 | 45 | 55 | 0.1 | 0.03 | 0 | ○ | ○ | 23 | 4 |
| Comparative Example 4 | 43 | 57 | 0.1 | 0.03 | 0 | ○ | Δ | 41 | 4 |
| Comparative Example 5 | 40 | 60 | 0.1 | 0.03 | 0 | ○ | Δ | 65 | 4 |
| Comparative Example 6 | 20 | 80 | 0.1 | 0.03 | 0 | ○ | Δ | 74 | 4.1 |
| Comparative Example 7 | ☐ | 100 | 0.1 | 0.03 | 0 | ○ | Δ | 128 | 4.1 |

Example 5

A curable composition was prepared in the same manner as in Example 1 but using 0.1 part by mass of the photo acid generator (IMDPI), 0.03 parts by mass of camphorquinone (CQ), and 0.03 parts by mass of ethyl 4-dimethylaminobenzoate (DMBE) as polymerization initiators, and was evaluated for its properties. The results were as shown in Table 2.

Examples 6 to 8 and Comparative Examples 8 to 13

Curable compositions were prepared in the same manner as in Example 5 but varying the ratio of blending the oxetane compound (OX-1) and the epoxy compound (EP-1) in a manner to accomplish the ratios of functional groups as shown in Table 2, and were evaluated for their properties. The results were as shown in Table 2.

TABLE 2

| | Cationically polymeriable monomer Ratio of functional groups | | Polymerization initiator Parts by mass | | | Surface state of cured product | | Curing time | Contraction by polymerization |
|---|---|---|---|---|---|---|---|---|---|
| | Oxetane compound | Epoxy compound | | | | | | | |
| | OX-1 | EP-1 | IMDPI | DMBAn | CQ | Condition 1 | Condition 2 | (sec) | (%) |
| Comparative Example 8 | 100 | ☐ | 0.1 | 0.03 | 0.03 | ○ | X | 92 | 3.8 |
| Comparative Example 9 | 95 | 5 | 0.1 | 0.03 | 0.03 | ○ | X | 61 | 3.8 |
| Comparative Example 10 | 92 | 8 | 0.1 | 0.03 | 0.03 | ○ | Δ | 35 | 3.8 |
| Example 5 | 90 | 10 | 0.1 | 0.03 | 0.03 | ○ | ○ | 25 | 3.9 |
| Example 6 | 80 | 20 | 0.1 | 0.03 | 0.03 | ○ | ○ | 23 | 3.9 |
| Example 7 | 55 | 45 | 0.1 | 0.03 | 0.03 | ○ | ○ | 19 | 3.9 |
| Example 8 | 45 | 55 | 0.1 | 0.03 | 0.03 | ○ | ○ | 28 | 4 |
| Comparative Example 11 | 43 | 57 | 0.1 | 0.03 | 0.03 | ○ | Δ | 50 | 4 |
| Comparative Example 12 | 40 | 60 | 0.1 | 0.03 | 0.03 | ○ | Δ | 69 | 4 |
| Comparative Example 13 | 20 | 80 | 0.1 | 0.03 | 0.03 | ○ | Δ | 80 | 4.1 |

As will be obvious from the results of Tables 1 and 2, the compositions having the oxetane functional groups and the epoxy functional groups at ratios lying in a range specified by the present invention, did not leave unpolymerized portion on the surface and could be cured within short periods of time even under highly humid conditions (condition 2), which were favorable properties enabling the compositions to be favorably used for dental purpose in the oral cavity.

On the other hand, when the amount of the oxetane functional groups was increased causing the ratio of the oxetane functional groups and the epoxy functional groups to lie outside the range specified by the present invention, an unpolymerized layer was formed on the surface under the highly humid conditions (condition 2). Further, when the amount of the epoxy functional groups was increased, the curing time was lengthened. Further, as will be understood from the comparison of the results of Table 1 with the results of Table 2, the effect of the invention was not affected even by changing the polymerization initiators from which it will be learned that the effect of the present invention is achieved by setting the ratio of particular functional groups to lie within a particular range.

Example 9

20 Grams of a mixture of spherical silica-zirconia (particle size of 0.5 μm) and spherical silica-titania (particle size of 0.1 μm) at a weight ratio of 7:3 was suspended in 80 ml of hydrochloric acid adjusted to pH of 4.0, and to which was added 1.2 g of 3-glycidyloxypropyltrimethoxysilane (silane coupling agent) with stirring. After stirred for one hour, water was distilled off by using an evaporator, and the obtained solid Was milled in a mortar and dried under a reduced pressure at 80° C. for 15 hours. After drying, the obtained powder was preserved as an inorganic filler (a) in a desiccator using silica gel as a drying agent.

On the other hand, like in Example 1, the oxetane compound (OX-1) and the epoxy compound (EP-1) were mixed together such that (a×A):(b:B)=90:10. To 100 parts by mass of the above mixture, there were added 0.1 part by mass of a photo acid generator (IMDPI), 0.03 parts by weight of a condensed polycyclic aromatic compound (DMBAn) and 0.03 parts by mass of camphorquinone (CQ) as polymerization initiators, and the mixture was stirred and dissolved until it became homogeneous thereby to prepare a curable composition.

The curable composition was mixed with the above inorganic filler (a) by using an agate mortar in a constant-temperature constant-humidity chamber maintained at a temperature of 22° C. and a humidity of 20% (content of inorganic filler: 76 mass %). The mixture was defoamed to remove bubbles in vacuum to thereby obtain a filler-containing curable composition (composite resin). The composite resin was evaluated for its microhardness after cured, curing time and coefficient of contraction by polymerization. The results were as shown in Table 3.

Examples 10 to 13 and Comparative Examples 14 to 19

Composite resins were prepared in the same manner as in Example 9 but varying the ratio of blending the oxetane compound (OX-1) and the epoxy compound (EP-1) in a manner to accomplish the ratios of functional groups as shown in Table 3, and were evaluated for their properties. The results were as shown in Table 3.

In the column of microhardness, "could not be measured" stands for that the cured product possessed a very brittle surface and its hardness was smaller than the lower limit of measurement of the microhardness tester (the same holds hereinafter in Tables 4 to 6, 10 and 11).

TABLE 3

| | Cationically polymeriable monomer Ratio of functional groups | | | | | |
|---|---|---|---|---|---|---|
| | Oxetane compound | Epoxy compound | Microhardness | | Curing time | Contraction by polymerization |
| | OX-1 | EP-1 | Condition 1 | Condition 2 | (sec) | (%) |
| Comparative Example 14 | 100 | — | 10 | could not be measured | 33 | 1.1 |
| Comparative Example 15 | 95 | 5 | 10 | could not be measured | 28 | 1.1 |
| Comparative Example 16 | 92 | 8 | 10 | 4 | 20 | 1.1 |
| Example 9 | 90 | 10 | 11 | 9 | 14 | 1.1 |
| Example 10 | 80 | 20 | 12 | 10 | 11 | 1.2 |
| Example 11 | 70 | 30 | 13 | 10 | 9 | 1.2 |
| Example 12 | 55 | 45 | 12 | 10 | 9 | 1.2 |
| Example 13 | 45 | 55 | 12 | 9 | 11 | 1.2 |
| Comparative Example 17 | 43 | 57 | 12 | 8 | 18 | 1.2 |
| Comparative Example 18 | 20 | 80 | 12 | 8 | 30 | 1.2 |
| Comparative Example 19 | — | 100 | 11 | 7 | 32 | 1.3 |

Examples 14 to 17 and Comparative Examples 20 to 24

Composite resins were prepared in the same manner as in Example 9 but using an oxetane compound (OX-2) instead of the oxetane compound (OX-1) and mixing it with the epoxy compound (EP-1) in a manner to accomplish the ratios of functional groups as shown in Table 4, and were evaluated for their properties. The results were as shown in Table 4.

TABLE 4

| | Cationically polymeriable monomer Ratio of functional groups | | Microhardness | | Curing time | Contraction by polymerization |
|---|---|---|---|---|---|---|
| | Oxetane compound | Epoxy compound | | | | |
| | OX-1 | EP-1 | Condition 1 | Condition 2 | (sec) | (%) |
| Comparative Example 20 | 100 | — | 11 | could not be measured | 30 | 1.2 |
| Comparative Example 21 | 95 | 5 | 12 | could not be measured | 27 | 1.2 |
| Comparative Example 22 | 92 | 8 | 12 | could not be measured | 18 | 1.2 |
| Example 14 | 90 | 10 | 12 | 10 | 13 | 1.3 |
| Example 15 | 80 | 20 | 12 | 11 | 10 | 1.3 |
| Example 16 | 60 | 40 | 12 | 11 | 9 | 1.3 |
| Example 17 | 45 | 55 | 13 | 10 | 10 | 1.3 |
| Comparative Example 23 | 43 | 57 | 12 | 10 | 17 | 1.3 |
| Comparative Example 24 | 20 | 80 | 11 | 10 | 30 | 1.3 |

Examples 18 to 21 and Comparative Examples 25 to 29

Composite resins were prepared in the same manner as in Example 9 but using an epoxy compound (EP-2) instead of the epoxy compound (EP-1) and mixing it with the oxetane compound (OX-1) in a manner to accomplish the ratios of functional groups as shown in Table 5, and were evaluated for their properties. The results were as shown in Table 5.

TABLE 5

| | Cationically polymeriable monomer Ratio of functional groups | | Microhardness | | Curing time | Contraction by polymerization |
|---|---|---|---|---|---|---|
| | Oxetane compound | Epoxy compound | | | | |
| | OX-1 | EP-2 | Condition 1 | Condition 2 | (sec) | (%) |
| Comparative Example 25 | 95 | 5 | 10 | could not be measured | 28 | 1.1 |
| Comparative Example 26 | 92 | 8 | 10 | could not be measured | 20 | 1.1 |
| Example 18 | 90 | 10 | 11 | 8 | 14 | 1 |
| Example 19 | 80 | 20 | 11 | 10 | 11 | 1 |
| Example 20 | 60 | 40 | 12 | 10 | 10 | 1 |
| Example 21 | 45 | 55 | 11 | 9 | 13 | 0.9 |
| Comparative Example 27 | 43 | 57 | 11 | 9 | 35 | 0.9 |
| Comparative Example 28 | 20 | 80 | 11 | 9 | 40 | 0.8 |
| Comparative Example 29 | — | 100 | 10 | 8 | 43 | 0.7 |

Comparative Examples 30 to 33

Composite resins were prepared in the same manner as in Example 9 but mixing cationically polymerizable compounds in a manner to accomplish the ratios of the functional groups as shown in Table 6, and were evaluated for their properties. The results were as shown in Table 6.

TABLE 6

| | Cationically polymeriable monomer Ratio of functional groups | | Microhardness | | Curing time | Contraction by polymerization |
|---|---|---|---|---|---|---|
| | Oxetane compound | Bicycloortho ester | | | | |
| | OX-1 | compound | Condition 1 | Condition 2 | (sec) | (%) |
| Comparative Example 30 | 80 | — | 20 | 7 | could not be measured | 10 | 1.1 |
| Comparative Example 31 | 55 | — | 45 | 6 | could not be measured | 12 | 1 |
| Comparative Example 32 | — | 80 | 20 | 8 | could not be measured | 9 | 1.2 |
| Comparative Example 33 | — | 55 | 45 | 6 | could not be measured | 10 | 1 |

Further, the composite resins prepared in Example 11 and in Comparative Examples 14 and 19 were measured for their flexural strengths and flexural moduli of elasticity to obtain results as shown in Table 7.

TABLE 7

| Composite resin | Flexural strength/MPa (Standard deviation) | Flexural modulus of elasticity/GPa (Standard deviation) |
|---|---|---|
| Composition of Example 11 | 119.3(3.1) | 10.2(0.83) |
| Composition of Comparative Example 14 | 119.1(3.8) | 11.8(0.89) |
| Composition of Comparative Example 19 | 118.8(4.0) | 10.9(0.95) |

The following Examples 22 to 37 use an oxetane compound and an alkenyl ether compound in combination as cationically polymerizable monomers (II).

Example 22

An oxetane compound (OX-1) and an alkenyl ether compound (DVE-1) were blended being so adjusted that the amount of (DVE-1) was 0.111 mols per mol of (OX-1) in an environment of a relative humidity of not higher than 20%. In this case, (OX-1) was a bifunctional oxetane compound and, hence, "a" was 2 while (DVE-1) was a bifunctional alkenyl ether compound and, hence, "b" was 2, establishing a relationship, $$(a \times A):(b \times B)=(2 \times 1):(2 \times 0.111)=90:10$$

By using the mixture of the above polymerizable monomers, a curable composition was prepared in quite the same manner as in Example 1.

The curable composition was evaluated for the surface state of the cured product and discoloration. The results were as shown in Table 8.

Examples 23, 24 and Comparative Examples 34 to 41

Curable compositions were prepared in the same manner as in Example 22 but varying the ratio of blending the oxetane compound (OX-1) and the alkenyl ether compound (DVE-1) in a manner to accomplish the ratios of functional groups as shown in Table 8, and were evaluated for their properties. The results were as shown in Table 8.

TABLE 8

| | Cationically polymeriable monomer Ratio of functional groups | | Surface state of the cured product | | Discoloration | |
|---|---|---|---|---|---|---|
| | Oxetane compound | Alkenyl ether compound | | | | Observed |
| | OX-1 | DVE-1 | Condition 1 | Condition 2 | $\Delta E^*$ | by eyes |
| Comparative Example 34 | 100 | — | ○ | X | 1 | ⊙ |
| Comparative Example 35 | 95 | 5 | ○ | X | 1 | ⊙ |
| Comparative Example 36 | 92 | 8 | ○ | Δ | 1 | ⊙ |
| Example 22 | 90 | 10 | ○ | ○ | 1.1 | ⊙ |
| Example 23 | 70 | 30 | ○ | ○ | 1.2 | ⊙ |
| Example 24 | 50 | 50 | ○ | ○ | 2.3 | ○ |

TABLE 8-continued

| | Cationically polymeriable monomer Ratio of functional groups | | Surface state of the cured product | | Discoloration | |
|---|---|---|---|---|---|---|
| | Oxetane compound | Alkenyl ether compound | | | | Observed |
| | OX-1 | DVE-1 | Condition 1 | Condition 2 | ΔE* | by eyes |
| Comparative Example 37 | 40 | 60 | ○ | ○ | 5 | X |
| Comparative Example 38 | 38 | 62 | ○ | Δ | 5.3 | X |
| Comparative Example 39 | 35 | 65 | ○ | Δ | 6 | X |
| Comparative Example 40 | 20 | 80 | ○ | Δ | 9.8 | X |
| Comparative Example 41 | — | 100 | ○ | Δ | 12 | X |

Example 25

A curable composition was prepared in the same manner as in Example 22 but using 0.1 part by mass of the photo acid generator (IMDPI), 0.03 parts by mass of camphorquinone (CQ), and 0.03 parts by mass of ethyl 4-dimethylaminobenzoate (DMBE) as polymerization initiators, and was evaluated for its property. The results were as shown in Table 9.

Examples 26, 27 and Comparative Examples 42 to 48

Curable compositions were prepared in the same manner as in Example 25 but varying the ratio of blending the oxetane compound (OX-1) and the alkenyl ether compound (DVE-1) in a manner to accomplish the ratios of functional groups as shown in Table 9, and were evaluated for their properties. The results were as shown in Table 9.

TABLE 9

| | Cationically polymeriable monomer Ratio of functional groups | | Surface state of the cured product | | Discoloration | |
|---|---|---|---|---|---|---|
| | Oxetane compound | Alkenyl ether compound | | | | Observed |
| | OX-1 | DVE-1 | Condition 1 | Condition 2 | ΔE* | by eyes |
| Comparative Examples 42 | 100 | — | ○ | X | 0.9 | ⊚ |
| Comparative Examples 43 | 95 | 5 | ○ | X | 0.9 | ⊚ |
| Comparative Example 44 | 92 | 8 | ○ | Δ | 1 | ⊚ |
| Example 25 | 90 | 10 | ○ | ○ | 1.1 | ⊚ |
| Example 26 | 70 | 30 | ○ | ○ | 1.2 | ⊚ |
| Example 27 | 50 | 50 | ○ | ○ | 2.3 | ○ |
| Comparative Example 45 | 40 | 60 | ○ | ○ | 5 | X |
| Comparative Example 46 | 38 | 62 | ○ | Δ | 5.4 | X |
| Comparative Example 47 | 35 | 65 | ○ | Δ | 6.1 | X |
| Comparative Example 48 | 20 | 55 | ○ | Δ | 9.7 | X |

As will be obvious from the results of Tables 8 and 9, the compositions having the oxetane functional groups and the alkenyl ether functional groups at ratios lying in a range specified by the present invention, did not leave unpolymerized portion on the surface (see evaluation of the surface state of the cured products) even under highly humid conditions (condition 2), which were favorable properties enabling the compositions to be favorably used for dental purposes in the oral cavity.

On the other hand, when the ratio of the oxetane functional groups and the alkenyl ether functional groups was deviated to lie outside the range specified by the present invention, there was formed an unpolymerized layer on the surface either when the amount of the oxetane functional groups was large or when the amount of the alkenyl ether functional groups was large. Further, as will be understood from the comparison of the results of Table 8 with the results of Table 9, the effect of the invention was not affected even by changing the polymerization initiators from which it will be learned that the effect of the present invention is achieved by setting the ratio of the functional groups to lie within a particular range.

Example 28

The oxetane compound (OX-1) and the alkenyl ether compound (DVE-1) were mixed together such that (a×A): (b:B)=90:10 in the same manner as in Example 22. To 100 parts by mass of the above mixture, there were added 0.1 part by mass of a photo acid generator (IMDPI), 0.03 parts by weight of a condensed polycyclic aromatic compound (DMBAn) and 0.03 parts by mass of camphorquinone (CQ) as polymerization initiators, and the mixture was stirred and dissolved until it became homogeneous thereby to prepare a curable composition.

The curable composition was mixed with the inorganic filler (a) prepared in Example 9 by using an agate mortar in a constant-temperature constant-humidity chamber maintained at a temperature of 22° C. and a humidity of 20% (content of the inorganic filler of 76 mass %). The mixture was defoamed to remove bubbles in vacuum to thereby obtain a filler-containing curable composition (composite resin). The composite resin was evaluated for its microhardness after cured and discoloration before and after curing. The results were as shown in Table 10.

Examples 29 to 31 and Comparative Examples 49 to 55

Composite resins were prepared in the same manner as in Example 28 but varying the ratio of blending the oxetane compound (OX-1) and the alkenyl ether compound (DVE-1) in a manner to accomplish the ratios of functional groups as shown in Table 10, and were evaluated for their properties. The results were as shown in Table 10.

TABLE 10

| | Cationically polymeriable monomer Ratio of functional groups | | | | | |
|---|---|---|---|---|---|---|
| | Oxetane compound | Alkenyl ether compound | Microhardness | | | Discoloration Observed |
| | OX-1 | DVE-1 | Condition 1 | Condition 2 | $\Delta E^*$ | by eyes |
| Comparative Example. 49 | 100 | — | 10 | could not be measured | 0.9 | ⊚ |
| Comparative Example 50 | 95 | 5 | 10 | could not be measured | 1 | ⊚ |
| Comparative Example 51 | 92 | 8 | 10 | 4 | 1 | ⊚ |
| Example 28 | 90 | 10 | 11 | 8 | 1 | ⊚ |
| Example 29 | 80 | 20 | 11 | 9 | 1 | ⊚ |
| Example 30 | 70 | 30 | 12 | 9 | 1.2 | ⊚ |
| Example 31 | 50 | 50 | 12 | 9 | 2.1 | ○ |
| Comparative Example 52 | 40 | 60 | 13 | 6 | 3.2 | ○ |
| Comparative Example 53 | 38 | 62 | 13 | 3 | 3.5 | X |
| Comparative Example 54 | 20 | 80 | 13 | could not be measured | 3.8 | X |
| Comparative Example 55 | — | 100 | 14 | could not be measured | 4.1 | X |

Examples 32 to 34 and Comparative Examples 56 to 61

Composite resins were prepared in the same manner as in Example 28 but using the oxetane compound (OX-2) instead of oxetane compound (OX-1) and mixing it with the epoxy compound (EP-1) in a manner to accomplish the ratios of functional groups as shown in Table 11, and were evaluated for their properties. The results were as shown in Table 11.

TABLE 11

| | Cationically polymeriable monomer Ratio of functional groups | | Microhardness | | Discoloration | |
|---|---|---|---|---|---|---|
| | Oxetane compound | Alkenyl ether compound | | | | Observed |
| | OX-1 | DVE-1 | Condition 1 | Condition 2 | ΔE* | by eyes |
| Comparative Example 56 | 100 | — | 11 | could not be measured | 1 | ◉ |
| Comparative Example 57 | 95 | 5 | 12 | could not be measured | 1.1 | ◉ |
| Comparative Example 58 | 92 | 8 | 12 | could not be measured | 1.1 | ◉ |
| Example 32 | 90 | 10 | 12 | 8 | 1.1 | ◉ |
| Example 33 | 70 | 30 | 12 | 9 | 1.2 | ◉ |
| Example 34 | 50 | 50 | 12 | 6 | 2.2 | ○ |
| Comparative Example 59 | 40 | 60 | 13 | 5 | 3.4 | ○ |
| Comparative Example 60 | 38 | 62 | 13 | 4 | 3.8 | X |
| Comparative Example 61 | 20 | 80 | 14 | could not be measured | 4.2 | X |

Examples 35 to 37 and Comparative Examples 62 to 67

Composite resins were prepared in the same manner as in Example 28 but using an alkenyl ether compound (DVE-2) instead of the alkenyl ether compound (DVE-1) and mixing it with the oxetane compound (OX-1) in a manner to accomplish the ratios of functional groups as shown in Table 12, and were evaluated for their properties. The results were as shown in Table 12.

TABLE 12

| | Cationically polymeriable monomer Ratio of functional groups | | Microhardness | | Discoloration | |
|---|---|---|---|---|---|---|
| | Oxetane compound | Alkenyl ether compound | | | | Observed |
| | OX-1 | DVE-2 | Condition 1 | Condition 2 | ΔE* | by eyes |
| Comparative Example 62 | 95 | 5 | 10 | could not be measured | 1 | ◉ |
| Comparative Example 63 | 92 | 8 | 10 | could not be measured | 1 | ◉ |
| Example 35 | 90 | 10 | 10 | 8 | 1.2 | ◉ |
| Example 36 | 70 | 30 | 10 | 9 | 1.2 | ◉ |
| Example 37 | 50 | 50 | 11 | 8 | 2.3 | ○ |
| Comparative Example 64 | 40 | 60 | 12 | 5 | 3.1 | ○ |
| Comparative Example 65 | 38 | 62 | 12 | 3 | 3.4 | X |
| Comparative Example 66 | 20 | 80 | 13 | could not be measured | 3.9 | X |
| Comparative Example 67 | — | 100 | 13 | could not be measured | 4.2 | X |

Further, the composite resins prepared in Example 32 and in Comparative Examples 49, 55 and 56 were measured for their flexural strengths and flexural moduli of elasticity to obtain results as shown in Table 13.

TABLE 13

| Composite resin | Flexural strength/MPa (Standard deviation) | Flexual modulus of elasticity/GPa (Standard deviation) |
| --- | --- | --- |
| Composition of Example 32 | 119.3(3.1) | 10.2(0.83) |
| Composition of Comparative Example 49 | 119.1(3.8) | 11.8(0.89) |
| Composition of Comparative Example 55 | 117.2(4.3) | 11.5(0.95) |
| Composition of Comparative Example 56 | 120.1(4.1) | 12.0(0.88) |

Ion the following Example 38 to 44, the oxetane compound and the epoxy compound were used in combination as cationically polymerizable monomers (II).

Example 38

To 60 parts by mass of OXT-1 and 40 parts by mass of EP-2, there were added 1.5 parts by mass of IMDPI, 0.2 parts by mass of DMBAn, 0.6 parts by mass of CQ, 0.1 part by mass of BHT and 0.1 part by mass of TN765 in a dark place, and the mixture was stirred and dissolved until it became homogeneous thereby to prepare a curable composition.

The curable composition was evaluated for the surface state of the cured product, its curing time and the number of days before it was gelled while being preserved at 50° C. The results were as shown in Table 14.

Example 39

To 60 parts by mass of OXT-1 and 40 parts by mass of EP-2, there were added 1.5 parts by mass of IMDPI, 0.2 parts by mass of DMBAn and 0.6 parts by mass of CQ in a dark place, and the mixture was stirred and dissolved until it became homogeneous thereby to prepare a curable composition.

The curable composition was evaluated for the surface state of the cured product, its curing time and the number of days before it was gelled while being preserved at 50° C. The results were as shown in Table 14.

Example 40

To 60 parts by mass of OXT-1 and 40 parts by mass of EP-2, there were added 1.5 parts by mass of IMDPI, 0.2 parts by mass of DMBAn, 0.6 parts by mass of CQ and 0.1 part by mass of BHT in a dark place, and the mixture was stirred and dissolved until it became homogeneous thereby to prepare a curable composition.

The curable composition was evaluated for the surface state of the cured product, its curing time and the number of days before it was gelled while being preserved at 50° C. The results were as shown in Table 14.

Example 41

To 60 parts by mass of OXT-1 and 40 parts by mass of EP-2, there were added 1.5 parts by mass of IMDPI, 0.2 parts by mass of DMBAn, 0.6 parts by mass of CQ and 0.1 part by mass of TN765 in a dark place, and the mixture was stirred and dissolved until it became homogeneous thereby to prepare a curable composition.

The curable composition was evaluated for the surface state of the cured product, its curing time and the number of days before it was gelled while being preserved at 50° C. The results were as shown in Table 14.

TABLE 14

| | Surface state of cured product | | Number of days preserved before gelled | Curing time (seconds) |
| --- | --- | --- | --- | --- |
| | Condition 1 | Condition 2 | | |
| Ex. 38 | ○ | ○ | 43 | 10 |
| Ex. 39 | ○ | ○ | 1 | 8 |
| Ex. 40 | ○ | ○ | 4 | 8 |
| Ex341 | ○ | ○ | 12 | 10 |

Example 42

50 Grams of spherical silica-zirconia (particle size of 0.21 μm) was suspended in 250 ml of ion-exchanged water. To this suspension, there was added 0.24 g of APS followed by vigorous stirring at room temperature for 30 minutes. To the suspension that has been stirred, there was added a mixture of 3.29 g of 3-glycidyloxypropyltrimethoxysilane and 100 ml of acetic acid aqueous solution (pH of 4.0) which has been stirred until it became homogeneous. After stirring, water was distilled off by using a rotary evaporator, and the obtained inorganic filler was further dried at 80° C. in vacuum to obtain a surface-treated inorganic filler.

The surface-treated inorganic filler and the curable composition of Example 39 were mixed together in an agate mortar (content of the surface-treated inorganic filler: 70 mass %). The mixture was defoamed in the same manner as in Example 9 to thereby obtain a composite resin.

The composite resin was evaluated for microhardness after curing, its curing time and the number of days before it was gelled while being preserved at 50° C. The results were as shown in Table 15.

Example 43

A composite resin was obtained in the same manner as in Example 42 by using the surface-treated inorganic filler used in Example 42 and the curable composition of Example 38.

The composite resin was evaluated for microhardness after curing, its curing time and the number of days before it was gelled while being preserved at 50° C. The results were as shown in Table 15.

Example 44

50 Grams of spherical silica-zirconia (particle size of 0.21 μm) was suspended in 250 ml of ion-exchanged water. To this suspension, there was added a mixture of 3.66 g of 3-glycidyloxypropyltrimethoxysilane and 100 ml of acetic acid aqueous solution (pH of 4.0) which has been stirred until it became homogeneous, followed by stirring at room temperature for 30 minutes. After stirring, water was distilled off by using a rotary evaporator, and the obtained inorganic filler was further dried at 80° C. in vacuum to obtain a surface-treated inorganic filler.

The surface-treated inorganic filler and the curable composition of Example 39 were mixed together in an agate mortar (content of the surface-treated inorganic filler: 70 mass %). The mixture was defoamed in the same manner as in Example 9 to thereby obtain a composite resin. The composite resin was evaluated for microhardness after curing, its curing time and the number of days before it was gelled while being preserved at 50° C. The results were as shown in Table 15.

TABLE 15

| | Microhardness | | Number of days preserved before gelled | Curing time (seconds) |
|---|---|---|---|---|
| | Condition 1 | Condition 2 | | |
| Ex. 42 | 12 | 10 | 30 | 12 |
| Ex. 43 | 11 | 10 | 49 | 13 |
| Ex. 44 | 12 | 11 | 1 | 10 |

The invention claimed is:

1. A cationically curable composition for dental use containing a cationic polymerization initiator (I) and cationically polymerizable monomers (II), wherein said cationically polymerizable monomers (II) contain an oxetane compound having an oxetane functional groups in the molecule thereof and an epoxy compound having an epoxy functional group in the molecule thereof or an alkenyl ether compound having an alkenyl ether functional group in the molecule thereof, at a ratio of amounts that satisfy the conditions expressed by the following formula, $$(a \times A):(b \times B) = 91:9 \text{ to } 45:55$$

wherein A is a mol number of said oxetane compound, "a" is an average number of the oxetane functional group contained in one molecule of said oxetane compound, B is a mol number of said epoxy compound or said alkenyl ether compound, and "b" is an average number of the epoxy functional group contained in one molecule of said epoxy compound or an average number of the alkenyl ether functional group contained in one molecule of said alkenyl ether compound.

2. A cationically curable composition for dental use according to claim 1, wherein said cationic polymerization initiator (I) contains a diaryliodonium salt compound, a condensed polycyclic aromatic compound and an oxidizable photo radical generator.

3. A cationically curable composition for dental use according to claim 2, wherein the diaryliodonium salt compound is contained in an amount of 0.001 to 10 parts by mass per 100 parts by mass of said cationically polymerizable monomers (II), the condensed polycycric aromatic compound is contained in an amount of 0.001 to 20 mols per mol of the diaryliodonium salt compound, and the oxidizable photo radical generator is contained in an amount of 0.001 to 20 mols per mol of the diaryliodonium salt compound.

4. A cationically curable composition for dental use according to claim 1, further containing a filler (III).

5. A cationically curable composition for dental use according to claim 3, wherein said filler (III) is contained in an amount of 50 to 1500 parts by mass per 100 parts by mass of said cationically polymerizable monomers (II).

6. A cationically curable composition for dental use according to claim 1, wherein said cationically curable composition is a filling/restorative material for dental use.

* * * * *